US010070950B2

(12) United States Patent
Piccagli et al.

(10) Patent No.: US 10,070,950 B2
(45) Date of Patent: Sep. 11, 2018

(54) ENDOLUMINAL PROSTHETIC ASSEMBLIES, AND ASSOCIATED SYSTEMS AND METHODS FOR PERCUTANEOUS REPAIR OF A VASCULAR TISSUE DEFECT

(71) Applicant: Medtronic Vascular, Inc., Santa Rosa, CA (US)

(72) Inventors: Francesco Piccagli, Roncadelle BS (IT); Jeffery Argentine, Petaluma, CA (US); Kieran Coghlan, Santa Rosa, CA (US); Carlo Guala, Roncadelle BS (IT); Massimo Morero, Roncadelle BS (IT); Darren Galligan, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 92 days.

(21) Appl. No.: 15/019,877

(22) Filed: Feb. 9, 2016

(65) Prior Publication Data

US 2017/0224467 A1   Aug. 10, 2017

(51) Int. Cl.
*A61F 2/07* (2013.01)
*A61F 2/958* (2013.01)
(Continued)

(52) U.S. Cl.
CPC .............. *A61F 2/07* (2013.01); *A61F 2/958* (2013.01); *A61F 2/966* (2013.01); *A61F 2/852* (2013.01);
(Continued)

(58) Field of Classification Search
CPC ........... A61F 2/07–2002/077; A61F 2002/826; A61F 2210/0061; A61F 2210/0085;
(Continued)

(56) References Cited

U.S. PATENT DOCUMENTS

| 2013/0103134 A1 | 4/2013 | Minion |
| 2013/0282103 A1 | 10/2013 | Madjarov et al. |
| 2014/0100650 A1 * | 4/2014 | Chobotov ................. A61F 2/07 623/1.35 |

FOREIGN PATENT DOCUMENTS

| WO | WO2011/158045 | 12/2011 | |
| WO | WO 2014172501 A2 * | 10/2014 | ............... A61F 2/07 |

OTHER PUBLICATIONS

Minion, David M.D. "Molded Parallel Endogralts for Branch Vessel Preservation During Endovascular Aneurysm Repair in Challenging Anatomy" International Journal of Angiology, vol. 21 No. 2/2012.
(Continued)

*Primary Examiner* — Yashita Sharma
*Assistant Examiner* — Rebecca Preston
(74) *Attorney, Agent, or Firm* — Medler Ferro Woodhouse & Mills PLLC

(57) ABSTRACT

A prosthetic assembly for repairing a target tissue defect within a target vessel region configured includes an exclusion structure sized to substantially bypass target tissue defect, and includes a branch assembly. The branch assembly can include a self-expanding outer branch prosthesis having an inflow region configured to deform to a non-circular cross-sectional-shape when deployed, and a support structure at least partially disposed within the inflow region. The support structure preserves blood flow to the branch vessel while the deformed inflow region inhibits blood leakage between and/or around the prosthetic assembly.

22 Claims, 28 Drawing Sheets

(51) Int. Cl.
  *A61F 2/966* (2013.01)
  *A61F 2/06* (2013.01)
  *A61F 2/852* (2013.01)
  *A61F 2/954* (2013.01)
  *A61F 2/95* (2013.01)
  *A61F 2/962* (2013.01)
  *A61F 2/82* (2013.01)

(52) U.S. Cl.
  CPC ............... *A61F 2/95* (2013.01); *A61F 2/954* (2013.01); *A61F 2/962* (2013.01); *A61F 2002/061* (2013.01); *A61F 2002/067* (2013.01); *A61F 2002/077* (2013.01); *A61F 2002/826* (2013.01); *A61F 2210/0014* (2013.01); *A61F 2210/0061* (2013.01); *A61F 2230/0006* (2013.01); *A61F 2230/0008* (2013.01); *A61F 2230/0069* (2013.01); *A61F 2250/0003* (2013.01); *A61F 2250/0004* (2013.01); *A61F 2250/006* (2013.01); *A61F 2250/0018* (2013.01); *A61F 2250/0039* (2013.01); *A61F 2250/0063* (2013.01); *A61F 2250/0069* (2013.01); *A61F 2250/0096* (2013.01)

(58) Field of Classification Search
  CPC ........ A61F 2250/0003; A61F 2250/006; A61F 2250/0069; A61F 2/856
  See application file for complete search history.

(56) References Cited

OTHER PUBLICATIONS

PCT/US2017/017252, The International Search Report and the Written Opinion of the International Searching Authority, dated Apr. 24, 2017.

\* cited by examiner

ENDOLUMINAL PROSTHETIC ASSEMBLIES, AND ASSOCIATED SYSTEMS AND METHODS FOR PERCUTANEOUS REPAIR OF A VASCULAR TISSUE DEFECT

FIELD OF THE INVENTION

The present technology relates generally to endoluminal prosthetic assemblies, and associated systems and methods for percutaneous repair of vascular tissue defects. In particular, several embodiments are directed to systems and devices to treat a blood vessel defect, such as an aneurysm and/or dissection, in a patient.

BACKGROUND OF THE INVENTION

Tissue defects within blood vessels, such as aneurysms (e.g., aortic aneurysms) or dissections, for example, can lead to pain (e.g., abdominal and back pain), stroke and/or eventual ruptures in the vessel. Aneurysms occur when there is a weakening in the wall of the blood vessel leading to a widening, opening or formation of a cavity within the vessel wall. The opening of such a cavity can be further exasperated by the continual interrogation from blood pooling in the cavity pressurizing the already weakened vessel wall. Such a damaged vessel, which can be age-related, drug or tobacco-induced, resulting from atherosclerosis or in some instances, caused by infection, can result in a vessel rupture leading to life-threatening internal bleeding.

Diseased or damaged blood vessels, such as those having aneurysms and/or dissections, can be non-invasively treated with endoluminal prosthetic devices or endografts that preserve blood flow through the damaged blood vessel. Many vascular aneurysms, dissections or other tissue defects occur in the aorta and peripheral arteries, and such minimally invasive surgical techniques have been developed to place exclusion devices within or across an opening or cavity associated with the subject tissue defect to prevent blood from further pressurizing the damaged vascular tissue. While conventional endograft devices can effectively span the diseased region and effectively seal off the opening or cavity from the remaining healthy or intact blood vessel, challenges arise when the diseased regions are in the vicinity of vessel bifurcations or "branch" vessels that continue to require blood flow to maintain other tissues or organs. For example, depending on the region of the aorta involved, an aneurysm may extend into segments of the aorta from which smaller branch arteries extend.

For example, abdominal aortic aneurysms include aneurysms present in the aorta distal to the diaphragm, e.g., pararenal aorta and the branch arteries that emanate therefrom, including the renal arteries and the superior mesenteric artery (SMA). Abdominal aortic aneurysms are bulges or weakening regions in the aortic wall and are frequently classified by their location relative to the renal arteries. Referring to FIGS. 1A-1C, various types of abdominal aortic aneurysms are shown for illustrative purposes. In FIGS. 1A-1C, a portion of an aorta A is shown extending down to the aortic bifurcation in which aorta A bifurcates into the common iliac arteries, including a right iliac artery RI and a left iliac artery LI. A right renal artery RRA and a left renal artery LRA extend from aorta A, as does the superior mesenteric artery (SMA) which arises from the anterior surface of the abdominal aorta. In FIG. 1A, an infrarenal abdominal aortic aneurysm $AAA_I$ is located distal to the renal arteries. In FIG. 1B, a juxtarenal abdominal aortic aneurysm $AAA_J$ approaches or extends up to, but does not involve, the renal arteries. In FIG. 1C, a suprarenal abdominal aortic aneurysm $AAA_S$ involves and extends above the renal arteries.

Various arrangements have been proposed and implemented to accommodate side branches, including main vessel stent-grafts having a fenestration or opening in a side wall that is positioned to align with the ostium of the branch vessel, and in some arrangements, further providing a branch vessel stent-graft that is deployed through the fenestration into the branch vessel to provide a prosthesis for blood flow into the branch vessel. While these prosthetic stent-graft devices offer minimally invasive methods for repairing vessel defects such as aneurysms and dissections, challenges remain to provide prosthetic stent-grafts that accommodate branch vessels and that prevent leakage into the tissue defect. For example, accommodating branch vessels emanating from the aorta can present numerous challenges due to differing anatomies and etiologies presented by individual patients. The varying shapes, locations, sizes and other features associated with an abnormal or unhealthy aorta can prevent proper alignment and/or sealing of the fenestration or branch stent-graft extending there-through with the vessel wall/tissue. Similarly, blood leakage can result from post-implantation migration or movement of the stent-graft causing misalignment between the fenestration(s) and the branch artery(ies), which may also result in impaired flow into the branch artery(ies).

Other techniques for accommodating side branch vessels include the use of multiple stent-grafts placed side by side in the seal zone. This technique, known as "snorkel" or chimney technique ("chEVAR" ("chimney endovascular aortic repair")), is an alternative approach to fenestrated/branched grafts. The chEVAR technique may utilize a main endoprosthesis 10 (FIGS. 1D-1F) used to treat the vascular pathology and deployed in the aorta, combined with separate stent-grafts 30 (chimneys) positioned between the aortic wall and main endoprosthesis 10, with a distal end of the stent-grafts/chimneys extending into the side branch vessels. However, as shown in FIGS. 1D-1F, gaps or gutters G are formed between main endoprosthesis 10, the wall W of the aorta, and the chimney stent-grafts 30. These gutters form a potential communication or flow path between the aorta and the opening or cavity of the diseased region (e.g. aneurismal region) of the aorta, thereby increasing pressure exerted in the diseased region. As can be seen in FIG. 1F, if the proximal portions of the chimney stent-grafts 30 deform to better conform to the gutters G, there is a risk that the deformation of the chimney stent-grafts 30 causes reduced patency of the lumen of the chimney stent-grafts 30, thereby reducing or blocking blood flow into the branch vessels.

BRIEF SUMMARY OF THE INVENTION

Embodiments hereof are directed to endoluminal prosthetic assemblies, and associated systems and methods for percutaneous repair of vascular tissue defects, such as aortic aneurysms and/or dissections. In various arrangements, prosthetic assemblies for repairing a target issue defect within a target region in a patient may include an exclusion structure sized to substantially cover the target tissue defect in the target vessel region when the exclusion structure is in a deployed configuration. The prosthetic assembly can also include a branch assembly for directing fluid flow to a branch vessel from the target vessel region. In one embodiment, the branch assembly can include an outer branch prosthesis having a first portion and second portion, wherein the first portion is configured to be deployed between the exclusion structure and a wall of the target vessel region, and the second portion is configured to be deployed in a branch vessel branching from the target vessel region. The branch assembly can further include a support structure at least partially disposed within the outer branch prosthesis at the first portion when the branch assembly is in a deployed configuration. In some embodiments, an inflow region of the first portion of the branch stent is expandable to a cross-sectional dimension larger than a cross-sectional dimension of the support structure, and in some embodiments, the first portion is deformable to a non-circular cross-sectional shape when deployed.

In other embodiments, a system to treat a blood vessel defect in a patient can include a prosthetic stent-graft device having an exclusion structure for bypassing the blood vessel defect in a main blood vessel. The prosthetic stent-graft device can also include a branch assembly configured to direct blood flow into one or more branch blood vessels from the main blood vessel while inhibiting leakage of blood into the blood vessel defect. In some arrangements, the branch assembly includes an outer branch stent-graft configured to self-expand to form a blood flow path from a proximal portion of the device in the main blood vessel to the branch blood vessel when the branch assembly is in a deployed configuration. The outer branch stent-graft can have an inflow region with a first cross-sectional dimension at a first portion and a second portion with a second cross-sectional dimension less than the first cross-sectional dimension. The branch assembly can also include an inner support structure at least partially disposed within the first portion of the outer branch stent-graft. The inner support structure can have a third cross-sectional dimension less than the first cross-sectional dimension. In certain arrangements, the first portion of the outer branch stent-graft has a first outward-oriented radial strength and the inner support structure has a second outward-oriented radial strength greater than the first outward-oriented radial strength. The system may also additionally include a delivery catheter having a lumen configured to retain at least the branch assembly in a delivery configuration, wherein the delivery configuration can have a lower profile than the deployed configuration.

In yet another aspect, embodiments of the present technology provide a method for repairing a target tissue defect in a blood vessel of a patient. The method can include positioning a branch assembly in a radially-contracted configuration within a region of the blood vessel having the target tissue defect, wherein a distal segment of the branch assembly is disposed within a branch vessel and a proximal segment of the branch assembly is disposed within the blood vessel. The branch assembly can include an outer branch stent-graft having an inflow region at the proximal segment, and an inner support structure configured to be at least partially disposed within the inflow region at the proximal segment of the branch assembly. The method can also include positioning an exclusion structure in the blood vessel, wherein at least a proximal portion of the exclusion structure is adjacent to the proximal segment of the branch assembly in the blood vessel, and wherein a central portion of the exclusion structure is aligned with the target tissue defect in the blood vessel. The method can further include expanding the exclusion structure in the blood vessel such that the central portion bypasses the target tissue defect, and expanding the branch assembly to a deployed configuration. In some embodiments, the proximal portion of the exclusion structure at least partially deforms the inflow region of the outer branch stent-graft without substantially deforming the inner support structure.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

DETAILED DESCRIPTION OF THE INVENTION

Figure 1A:
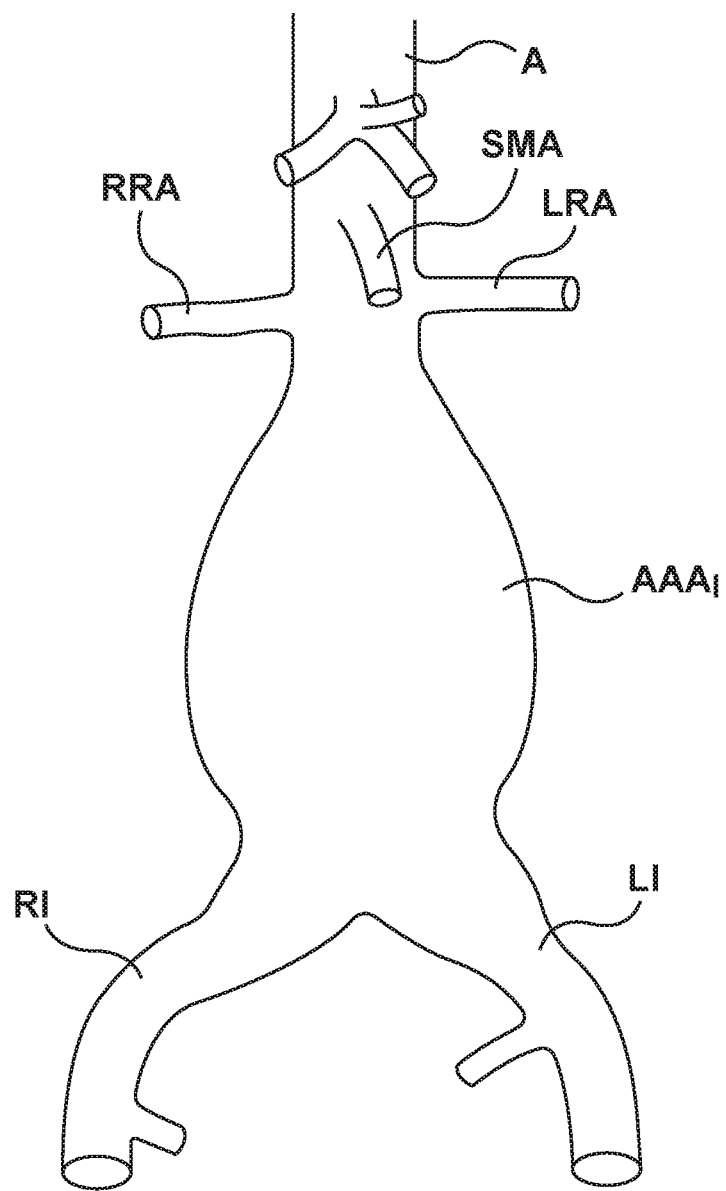
FIGS. 1A-1C are schematic illustrations of various types of abdominal aortic aneurysms.

Specific embodiments of the present technology are now described with reference to the figures, wherein like reference numbers indicate identical or functionally similar elements. Unless otherwise indicated, the terms "distal" and "proximal" are used in the following description with respect to the direction of blood flow from the heart and through the vasculature. Accordingly, with respect to a prosthetic assembly, the terms "proximal" and "distal" can refer to the location of portions of the device with respect to the direction of blood flow. For example, proximal can refer to an upstream position or a position of blood inflow, and distal can refer to a downstream position or a position of blood outflow. For example, "distal" or "distally" indicates an apparatus portion distant from, or a direction away from the heart or along the vasculature in the direction of blood flow. Likewise, "proximal" and "proximally" indicates an apparatus portion near to, or in a direction towards the heart.

The following detailed description is merely exemplary in nature and is not intended to limit the present technology or the application and uses of the present technology. Although the description of embodiments hereof are in the context of treatment of tissue defects in blood vessels, the present technology may also be used in any other body passageways or other blood vessel locations not specifically discussed herein and where it is deemed useful (e.g., other anatomical lumens, such as bronchial and other air passageways, fallopian tubes, bile ducts, etc.). Furthermore, there is no intention to be bound by any expressed or implied theory presented in the preceding technical field, background, brief summary or the following detailed description.

Embodiments of the present technology as described herein can be combined in many ways to treat one or more of many vascular defects such as aneurysms or dissections within a blood vessel, such as the abdominal aorta. The embodiments of the present technology can be therapeutically combined with many known surgeries and procedures, for example, such embodiments can be combined with known methods of accessing the target tissue defects, such as percutaneous access of the abdominal aorta through the femoral artery to deliver and deploy the prosthetic assemblies described herein. Other routes of access to the target regions are also contemplated and are well known to one of ordinary skill in the art.

As discussed herein, the aneurysmal region of the aorta can be bypassed by use of an endoluminally delivered tubular exclusion device, such as a stent-graft, placed inside the vessel and spanning the aneurysmal portion of the vessel to seal off the aneurysmal portion from further exposure to blood flowing through the aorta. A stent-graft, which normally includes a stent covered or lined by a graft or sealing material, can be delivered transluminally (e.g., introduced through the femoral artery) and implanted using specialized delivery catheters. The use of stent-grafts to internally bypass the aneurysmal region effectively requires that the stent-graft be positioned such that the proximal and distal ends of the stent-graft provide an occlusive seal when in contact with healthy portions of the vessel. The aforesaid challenges include providing critical branch arteries with sufficient blood flow, regardless if the ostium of those arteries originate within or immediately adjacent to aneurysmal (or defect vessel) site, or whether they are located within one of the zones required for sealing the main stent-graft to the wall of the aorta.

Figure 1B:
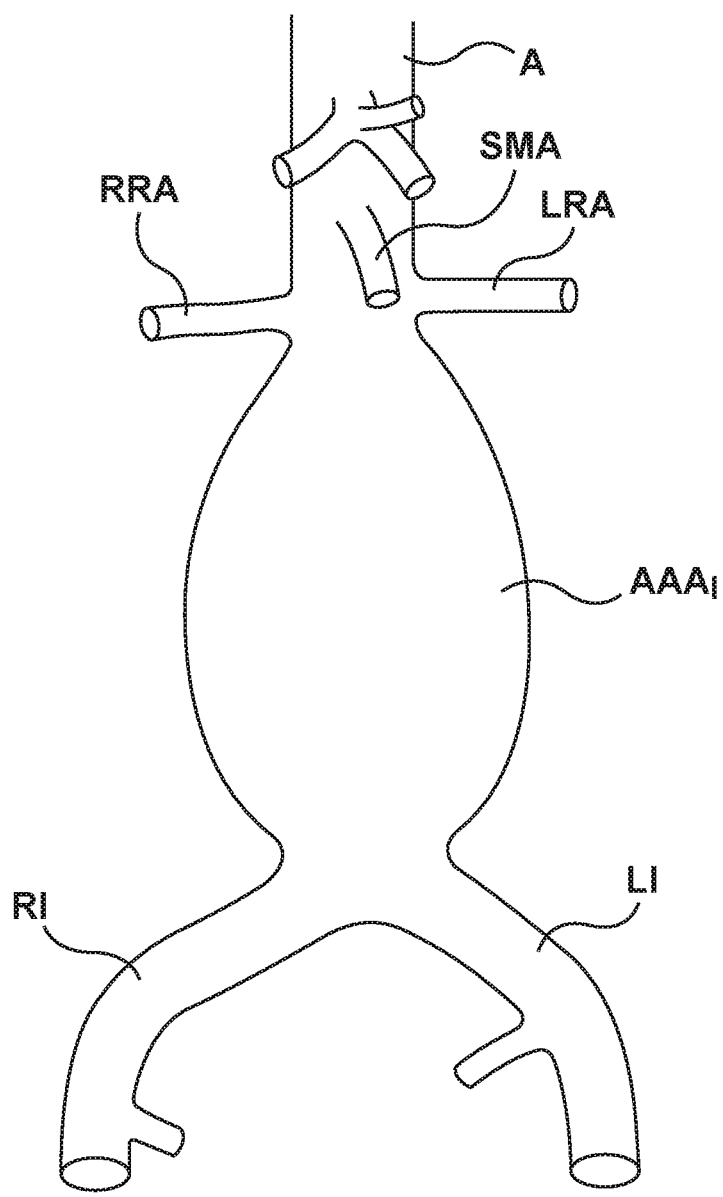
Figure 1C:
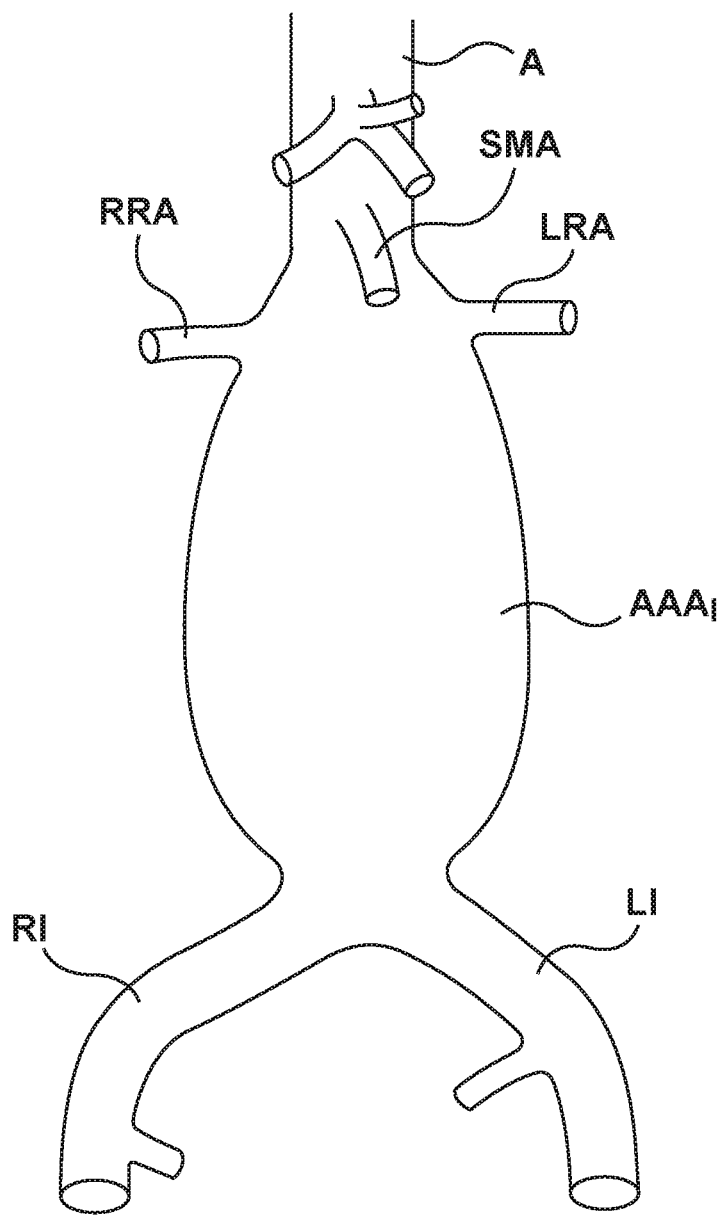

Particular issues arise in treating juxtarenal abdominal aortic aneurysms, as shown in FIG. 1B, and suprarenal abdominal aortic aneurysms, shown in FIG. 1C. Similar issues arise in treating so-called short-neck infrarenal aneurysms, in which only a small length (i.e., less than 10 mm) of non-aneurysed tissue is present between the renal arteries and the proximal end of the infrarenal aneurysm. Often, a proximal infrarenal neck or non-aneurysmal tissue of 10-15 mm length is usually required to allow endovascular repair of abdominal aortic aneurysms (EVAR). Since juxtarenal and suprarenal aneurysms extend up to or above the renal arteries, there is an insufficient non-aneurysmal length or neck of the aorta distally of (i.e., distal to or downstream of) the renal arteries for a stent-graft to deploy and seal against the vessel wall. Accordingly, it is necessary to deploy some of the stent-graft proximally of (i.e., above or upstream of) the renal arteries, which requires consideration of the superior mesenteric artery (SMA) and not to occlude or block blood flow to the renal arteries or the SMA.

Embodiments of endoluminal prosthetic assemblies, delivery systems and associated methods in accordance with the present technology are described in this section with reference to FIGS. 2A-11G. It will be appreciated that specific elements, substructures, uses, advantages, and/or other aspects of the embodiments described herein and with reference to FIGS. 2A-11G can be suitably interchanged, substituted or otherwise configured with one another in accordance with additional embodiments of the present technology.

Provided herein are systems, devices and methods suitable for percutaneous delivery and implantation of endoluminal prosthetic assemblies in a blood vessel of a patient. In some embodiments, methods and devices are presented for the treatment of vascular diseases, such as aneurysms and dissections, by minimally invasive implantation of artificial or prosthetic assemblies, including stent-graft assemblies. For example, an endoluminal prosthetic assembly, in accordance with embodiments described herein, can be implanted for repair (e.g., exclusion or bypassing) of a diseased or damaged segment of the aorta in a patient, such as in a patient suffering from abdominal aortic aneurysms as illustrated in FIGS. 1A-1C. In further embodiments, the prosthetic assembly is suitable for implantation and repair (e.g., exclusion or bypass) of other diseased or damaged blood vessels or other suitable anatomical lumens.

Figure 2A:
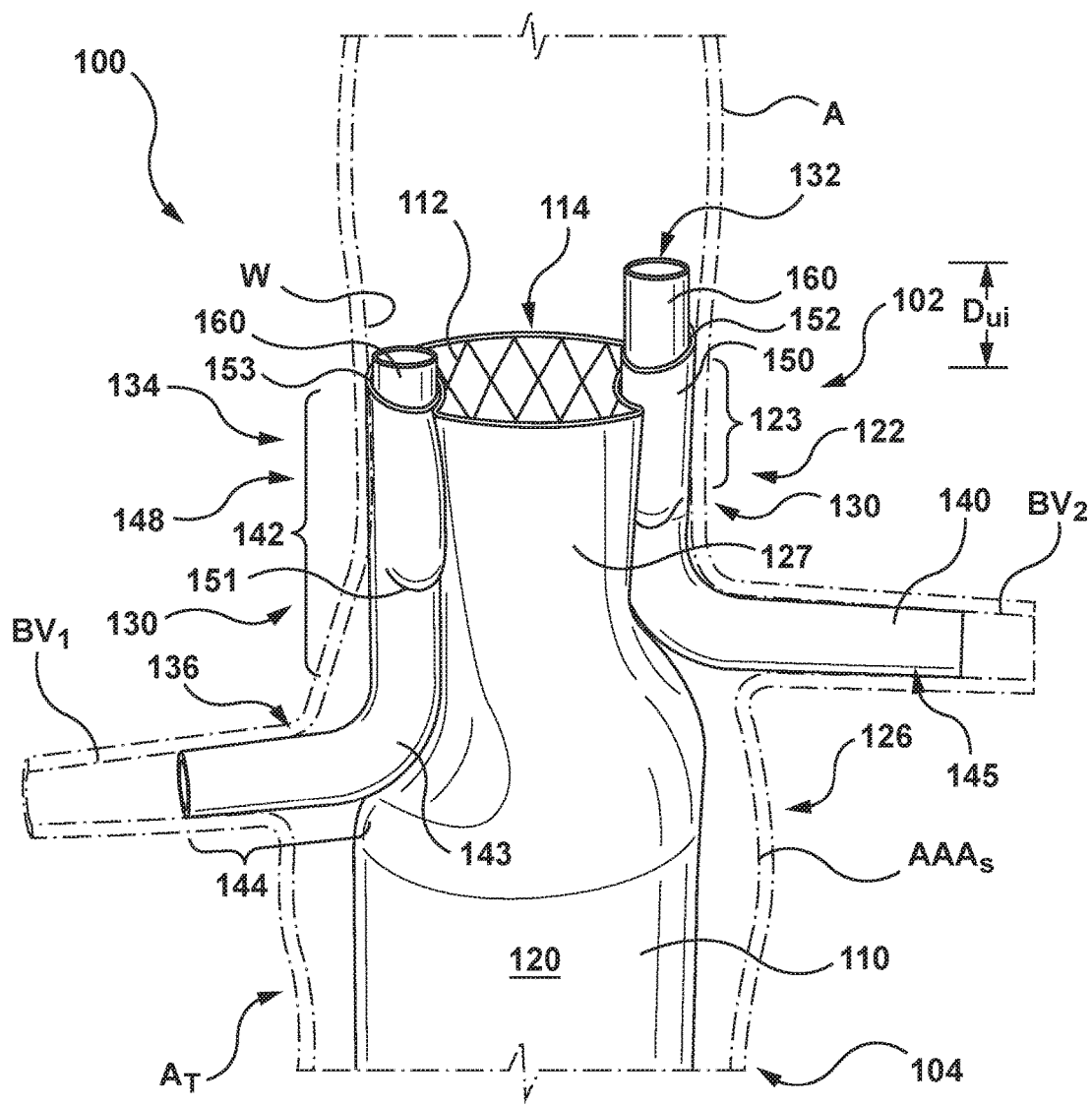
FIG. 2A illustrates a partial transparent view of an aorta displaying an abdominal aortic aneurysm and showing a prosthetic assembly implanted within the aorta at a target vessel region in accordance with an embodiment of the present technology.

FIG. 2A illustrates a partial transparent view of an aorta A displaying a suprarenal abdominal aortic aneurysm $AAA_S$ and showing a prosthetic assembly 100 implanted within the aorta at the target vessel region $T_R$ in accordance with an embodiment of the present technology.

The prosthetic assembly 100 can be movable between a radially-contracted or delivery configuration (see. e.g., FIG. 8B), a radially-expanded configuration (not shown), and a deployed configuration (shown in FIG. 2A). In the radially-contracted configuration, the prosthetic assembly 100 has a low profile suitable for delivery through small-diameter guide catheters positionable within the aorta and branch vessels thereof via approach through, for example, the femoral artery. As used herein, "radially-expanded configuration" refers to the configuration of the device/assembly when allowed to freely expand to an unrestrained size without the presence of constraining or distorting forces. "Deployed configuration" or "radially-expanded deployed configuration" as used herein, refers to the device/assembly once expanded at the target vessel site and subject to the constraining and distorting forces exerted by the native anatomy of the vessels and/or the other prosthetic assembly components.

In addition, many of the structures or components of the prosthetic assembly 100 as described herein utilize stent structures. These stent structures can be self-expanding and/or balloon expandable as is known in the relevant art. The term "self-expanding" is used in the following description with reference to one or more stent structures of the prostheses hereof and is intended to convey that the structures are shaped or formed from a material that can be provided with a mechanical memory to return the structure from a radially-compressed or constricted delivery configuration to a radially-expanded configuration for deployment. Non-exhaustive exemplary self-expanding materials include stainless steel, a super-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Figure 2B:
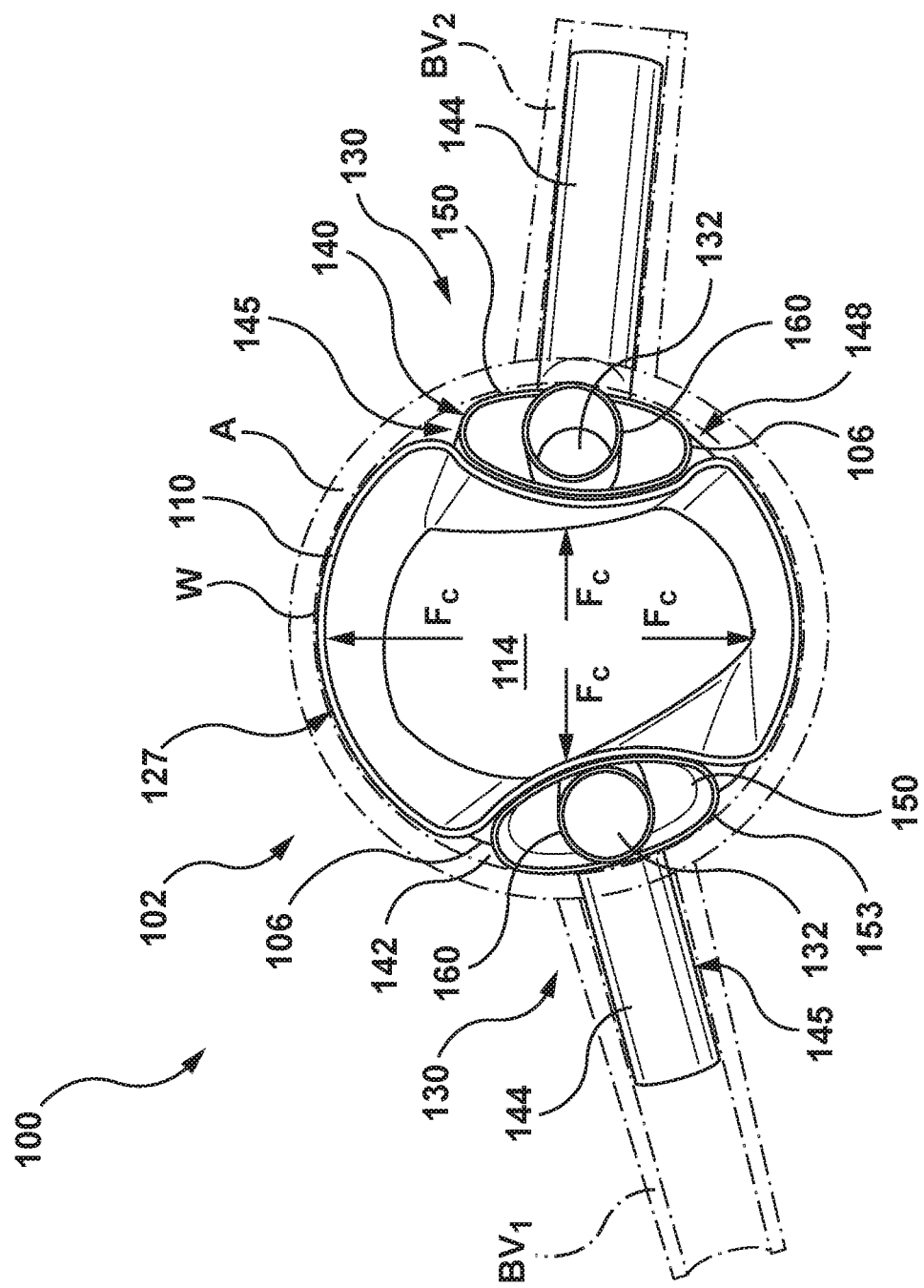
FIG. 2B is a top view of the prosthetic assembly of FIG. 2A in accordance with an embodiment of the present technology.

FIGS. 2A and 2B are partial side and top views, respectively, of a proximal portion of the prosthetic assembly 100 in a deployed configuration in accordance with an embodiment of the present technology. Referring to FIGS. 2A and 2B together, the prosthetic assembly 100 includes an expandable exclusion structure 110, which may also be referred to as a main vessel prosthesis or a main vessel stent-graft, and which is configured to isolate and/or exclude the diseased portion of the blood vessel (e.g., the aneurysm $AAA_S$) such that blood flow bypasses the aneurysm. The prosthetic assembly 100 further includes one or more branch assemblies 130 for directing blood flow to branch vessels $BV_1$, $BV_2$ (e.g., renal arteries RRA and LRA, or the SMA shown in FIG. 1C) from the main vessel (e.g., aorta A).

Figure 3:
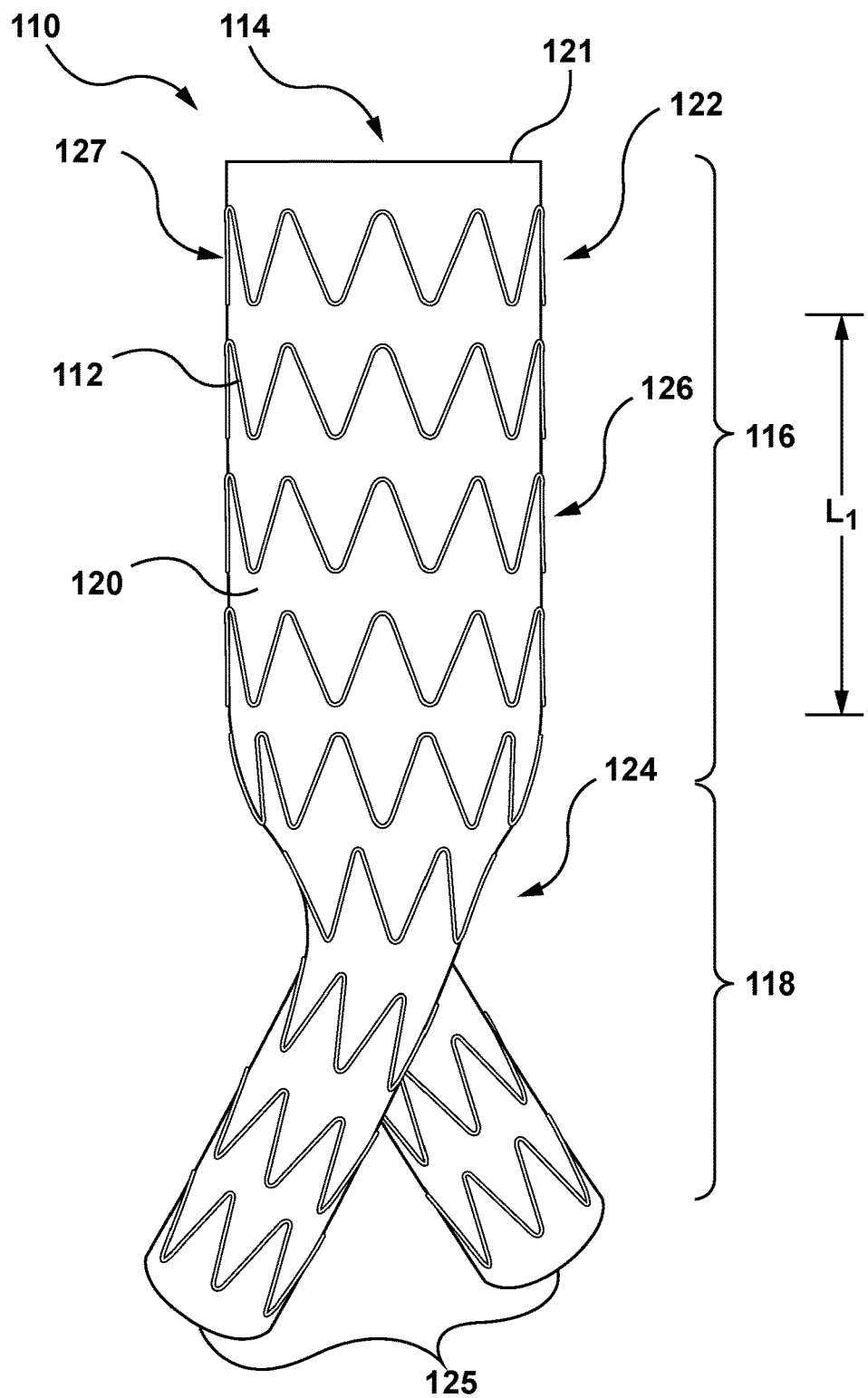
FIG. 3 is a side view an exclusion structure for use with the prosthetic assembly of FIG. 2A in accordance with an embodiment of the present technology.

With reference to FIGS. 2A-3, the exclusion structure 110 can be a stent-graft prosthesis including a frame 112 supporting a body 120. The frame 112 and the body 120 define a lumen 114 through which blood can flow. The body 120 may be, for example and not by way of limitation, a graft material as commonly used in stent-grafts. The frame 112 can be a stent or plurality of stents. The exclusion structure 110 is configured for placement in a main vessel such as the abdominal aorta A. FIGS. 2A and 2B illustrate a proximal portion of the exclusion structure 110 in a deployed configuration from a side and top perspective, respectively, and FIG. 3 illustrates an exemplary side view of the exclusion structure 110 in its radially-expanded (unbiased) configuration.

In an embodiment, with reference to FIG. 3, the exclusion structure 110 may include a main trunk segment 116 and distal bifurcated segment 118. In an embodiment, the bifurcated segment 118 is integrally formed with trunk segment 116 as a single or unitary prosthesis. In another arrangement, the bifurcated segment 118 may be formed separately from the trunk segment 116 and coupled thereto, or in other embodiments, may not be a present feature of the exclusion structure 110. When deployed in situ, the trunk segment 116 is configured for placement within the abdominal aorta A and the bifurcated segment 118 is configured for placement proximal to or above the aortic bifurcation of the right and left common iliac arteries. Although not shown, the exclusion structure 110 may also include a bare stent or seal stent or spring stent at a proximal end of the trunk segment 116, as known in the art.

Referring to FIG. 3, the exclusion structure 110 has a first end 121 at a proximal portion 122 that can define a proximal seal zone 123 with a healthy portion of the main vessel (FIG. 2A), and includes a distal portion 124 that defines a second end 125 along which defines a distal seal zone (not shown in FIG. 2A) with a healthy portion of the aorta distal to the tissue defect to be bypassed. Accordingly, the first and second ends 121, 125 are sufficiently spaced apart longitudinally such that a central portion 126, having an appropriate longitudinal length $L_1$, aligns with and seals off the target tissue defect (e.g., the aneurysm $AAA_S$) from the healthy portions of the main vessel. When the prosthetic assembly 100 is deployed, the central portion 126 of the exclusion structure 110 substantially covers the aneurysm $AAA_S$ (FIG. 2A), thereby excluding the defect tissue portion from blood flow through the vessel.

The body 120 of the exclusion structure 110 may be formed from any suitable graft or sealing material, for example and not limited to, a low-porosity woven or knit polyester, DACRON material, expanded polytetrafluoroethylene, polyurethane, silicone, ultra-high molecular weight polyethylene, or other suitable materials. In another embodiment, the graft material could also be a natural material such as pericardium or another membranous tissue such as intestinal submucosa. The graft or sealing material of the body 120 may overlay or line an inside surface of the frame 112. In some embodiments, the body 120 and/or the frame 112 together may be formed of layers of mesh that can include one or more braided or mesh layers that self-expand to a predetermined or pre-formed shape for providing a seal between the vessel tissue and an outer surface 127 of the exclusion structure 110 and/or between the branch assemblies 130 and the exclusion structure 110, as described further herein.

Referring to FIGS. 2A and 2B, the exclusion structure 110, when deployed in combination with one or more branch assemblies 130 within the main vessel (e.g., in the deployed configuration), is configured to selectively deform in a radially inward direction in regions contacting and/or adjacent to the branch assemblies 130. For example, the frame 112 of the exclusion structure 110 is configured to be sufficiently flexible to accommodate a branch assembly 130 that is deployed in parallel, while continuing to maintain a generally radially outward compressive force $F_C$, that ensures that the exclusion structure 110 is contacting and sealing against an inner wall W of the main vessel in regions not contacting and/or adjacent to such a branch assembly 130 (see FIG. 2B).

Referring again to FIGS. 2A and 2B, the prosthetic assembly 100 includes the one or more branch assemblies 130 that direct blood flow and perfuse branch vessels BV1, BV2 that branch from the main vessel (e.g., abdominal aorta A). In certain cases, one or more of the branch vessels BV1, BV2 may branch from the main vessel either within a seal zone (e.g., proximal seal zone 123, FIG. 2A) or within the diseased portion of the aorta A. As shown in FIG. 2A, the branch assembly 130 provides an internal conduit 132 through which blood can be directed from upstream of the target vessel region $T_R$ to a branch vessel BV. When deployed, a proximal segment 134 of each branch assembly 130 is disposed between the proximal portion 122 of the exclusion structure 110 and the internal vessel wall W. The internal conduit 132 of the branch assembly 130 permits blood to flow in a downstream direction from the proximal segment 134 and through a distal segment 136 of the branch assembly 130, thereby preserving blood flow to the branch vessel BV FIGS. 4A-4E include side, top and partial side views of an embodiment of a branch assembly 130 and components thereof in accordance with the present technology. Referring to FIGS. 2A-2B and 4A-4E together, the branch assembly 130 includes a flexible outer branch prosthesis 140 at least partially surrounding a separate inner support structure 160 disposed within a first portion 142 thereof. The outer branch prosthesis 140 can be a self-expanding stent-graft comprising an elongated, self-expanding scaffold, frame or stent 141 which can be covered and/or lined with a graft or sealing material 145. The outer branch prosthesis 140 includes the first portion 142, a mid-segment 143, and a second portion 144 opposite the first portion 142, that together, when deployed, can direct blood from the main vessel, through the proximal seal zone 123 and into the branch vessel BV using a "snorkel" or chimney technique for endovascular aortic aneurysm repair (chEVAR) (FIGS. 2A-2B). As shown in FIG. 2A, the first portion 142 of the outer branch prosthesis 140 is configured to be positioned and oriented in parallel to the proximal portion 122 of the exclusion structure 110 when deployed within the main vessel (e.g., aorta A). As described further herein, the first portion 142 includes an inflow region 150 at an upstream portion 148 thereof that is configured to be deformed such that a deployed cross-sectional profile of the inflow region 150 is influenced by surrounding compressive forces exerted by the exclusion structure 110 and the internal wall W of the main vessel. As the inflow region 150 deforms during deployment, patency of a lumen 154 of the outer branch prosthesis, and thus the internal conduit 132 of the branch assembly 130, is maintained by the support structure 160 that is at least partially disposed within the first portion 142 and at least within the inflow region 150 (FIG. 2B). The outer branch prosthesis 140 is further configured to bend or curve through the mid-segment 143 to form an elbow such that the second portion 144 can be deployed within the branch vessel BV (FIG. 2A).

In accordance with aspects of the present technology, the proximal or first portion 142 of the outer branch prosthesis 140, while in a deployed configuration, is sufficiently radially flexible such that the outer branch prosthesis 140 conforms to the irregularly-shaped or non-circular-shaped space created between a deployed, deformed exclusion structure 110 and internal wall W of the main vessel. Accordingly, this conformation of the outer branch prosthesis 140 effectively fills the gutters or gaps G (see FIGS. 1D-1F) between the deployed, deformed exclusion structure 110 and the internal wall W, thereby sealing the prosthetic assembly 100 against the internal wall W to anchor the prosthetic assembly 100 and to prevent leaks that can typically occur when using side-by-side stent-grafts. Further, in order to maintain patency of the lumen 154 of the first portion of the outer branch prosthesis 140 such that sufficient blood flows to the branch vessels BV, the support structure 160 may be more rigid and/or have hoop strength or radial resistance greater than the radial resistance of at least the first portion 142 of the outer branch prosthesis 140 (or the inflow region 150). In some embodiments, the support structure 160 has a radial resistance of at least 50%, or in other embodiments at least 100%, and in further embodiments at least 500% or at least 1000% greater than a radial resistance of the first portion 142 of the outer branch prosthesis 140. In embodiments, the support structure 160 has a radial strength or resistance to radial compression greater than the compressive force $F_C$ exerted by the exclusion structure 110 (FIG. 2B). In other embodiments, the support structure 160 can have a radial strength or resistance to radial compression the same as or even less than the radial strength of the inflow region 150 of the outer branch prosthesis 140. However, in such embodiments, the radial strength of the support structure 160 in addition to the radial strength of the inflow region 150 of the outer branch prosthesis 140 is sufficient to maintain patency of the internal conduit 132.

Referring back to FIG. 4A, the frame 141 can be constructed from a self-expanding or spring material, such as nitinol, and have sufficient radial spring force and flexibility to conformingly engage the sealing material 145 of the outer branch prosthesis 140 with the blood vessel inner wall in order to avoid excessive leakage, and prevent pressurization of the aneurysm (e.g., to provide a leak-resistant seal). The graft or sealing material 145 can be, for example, expanded polytetrafluoroethylene, a low-porosity woven or knit polyester, DACRON material, polyurethane, silicone, ultra-high molecular weight polyethylene, or other suitable materials. In other arrangements, the outer branch prosthesis 140 may have other configurations, including but not limited to balloon-expandable frames, or in which the sealing material 145 may be formed of layers of mesh (e.g., one or more braided or mesh layers), such as wire mesh having mechanical memory that self-expands to a predetermined or preformed shape for providing a seal or occlusive property.

Figure 4A:
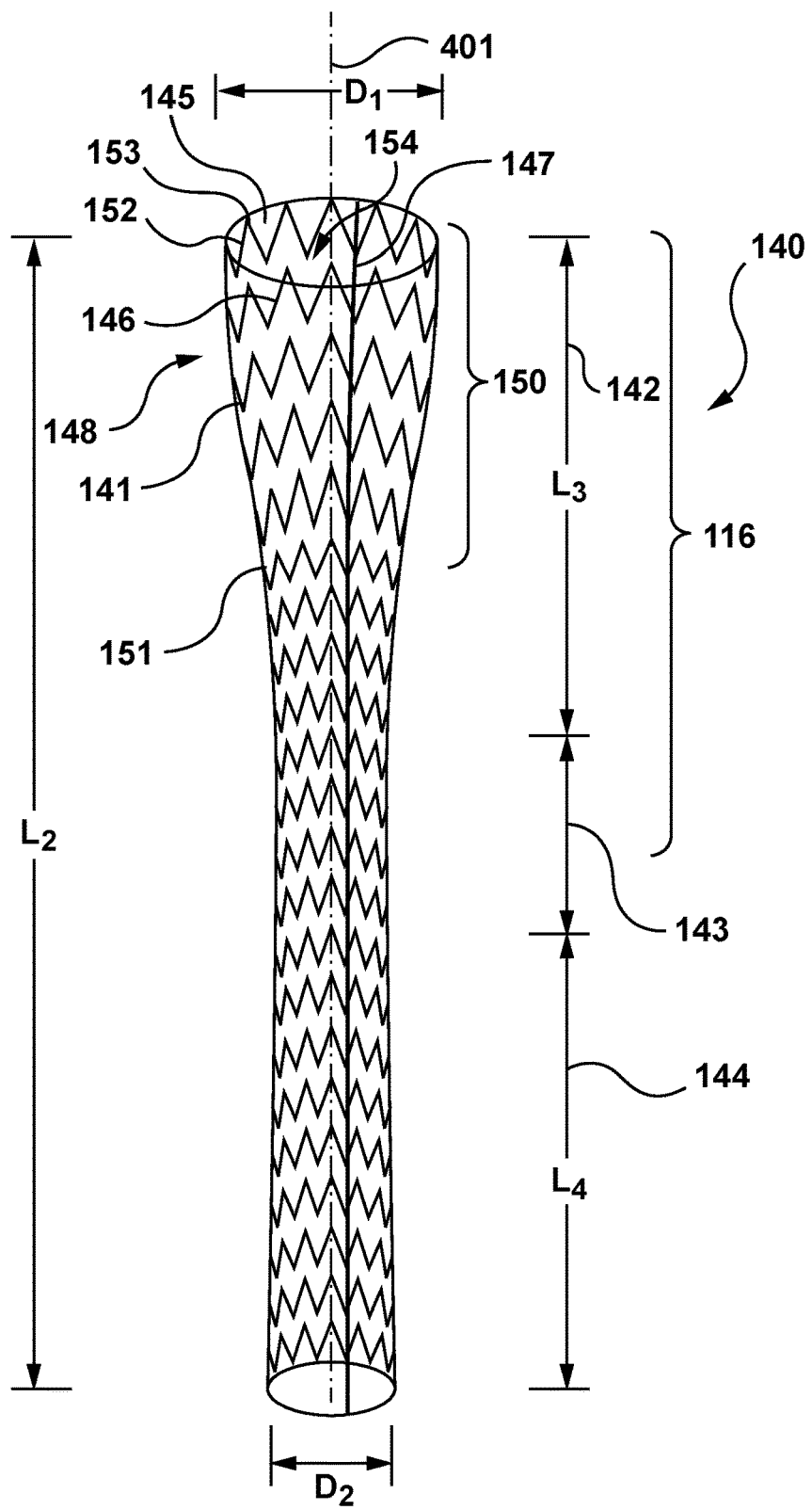
FIG. 4A is a side view of a self-expanding outer branch prosthesis for use in a branch assembly and in accordance with an embodiment of the present technology.

As illustrated in FIG. 4A, the outer branch prosthesis 140, when in a radially-expanded configuration, has the first portion 142 and the second portion 144 opposite the first portion 142 relative to a longitudinal axis 401 of the radially-expanded outer branch prosthesis 140. The first portion 142 of the outer branch prosthesis 140, such as the inflow region 150, can have a larger radial dimension than the distal portion 144 of the outer branch prosthesis 140. In one embodiment the inflow region 150 of the outer branch prosthesis 140 has a generally frustoconical shape or "flared" side profile beginning at a transition 151 and progressively expanding radially outward until terminating at a proximal end 152, thereby forming a rim 153 of the outer branch prosthesis 140 that, when in the radially-expanded (i.e., unbiased) configuration (see FIGS. 4A and 4C), can be substantially circular in cross-section and have a first radial cross-sectional dimension $D_1$. The outer branch prosthesis 140, in portions distal to the transition 151 (e.g., a distal portion of the first portion 142, the mid-segment 143, the second portion 144) can be substantially circular in cross-section and have a second radial cross-sectional dimension $D_2$ that is less than the first radial cross-sectional dimension $D_1$. Alternatively, instead of a flared inflow region 150, the transition 151 may be a stepped transition such that the inflow region 150 has a substantially uniform first radial cross-sectional dimension $D_1$ and the portions distal to the transition 151 have a substantially uniform second radial cross-sectional dimension $D_2$ that is less than the first radial cross-sectional dimension $D_1$ (see FIG. 5A).

Generally, the outer branch prosthesis 140 can have an overall length $L_2$ that is sufficient to provide a fluid path from the proximal region 102 of the prosthetic assembly 100 into the branch vessel BV when deployed. A length $L_3$ of the first portion 142 provides for spanning the proximal seal zone 123 and to a distal position within the main vessel adjacent to the ostium of the branch vessel BV. The inflow region 150 comprises a portion of the length $L_3$ at the most proximal segment 134 of the branch assembly 130 (FIG. 2A). In certain embodiments, for example, the length $L_2$ of the outer branch prosthesis 140 can be approximately 80 mm and the length $L_3$ of the first portion 142 can be about 25 mm to about 40 mm with the inflow region 150 comprising about 20 mm to about 30 mm at the upstream portion 148. In other arrangements, the length $L_2$ of the outer branch prosthesis 140 can be other suitable lengths (e.g., about 30 mm to about 200 mm). In certain arrangements, the length $L_3$ can be about ⅛ to about ¾ the length $L_2$ of the outer branch prosthesis 140. Similarly, the second portion 144 can have a length $L_4$ suitable to anchor the outer branch prosthesis 140 within the branch vessel BV. In some embodiments, the length $L_4$ of the second portion 144 can be about 20 mm to about 100 mm.

In some embodiments, the frame 141 of the outer branch prosthesis 140 can include a series of circumferential struts 146 which, in some embodiments, are connected longitudinally by circumferentially spaced-apart, resiliently deformable and flexible longitudinal posts 147. In other arrangements, longitudinal posts are not included in the frame 141. In embodiments having two or more longitudinal posts 147, the frame 141 of the first portion 142 of the outer branch prosthesis 140 may exhibit one or more preferential orienting planes such that the first portion 142 may self-orient inside the main vessel and the inflow region 150 can assume a desired cross-sectional profile when deployed with an adjacent exclusion structure 110. In a particular embodiment, the frame 141 of the outer branch prosthesis 140 can include four longitudinal posts 147 positioned approximately 90° from each other longitudinal post around a circumference 155 of the frame 141 (see FIG. 4C). In this example, the load exerted upon the first portion 142 of the outer branch prosthesis 140 by the proximal portion 122 of the exclusion structure 110 when deployed within the main vessel, would cause the inflow region 150 to assume an elliptical or oval cross-sectional profile. Other arrangements, including one, two, three, or more than four longitudinal posts 147 positioned about the circumference 155 of the frame 141 (e.g., for pre-determining one or more preferential orienting planes of deformation) are also contemplated. Likewise, the frame 141 can be formed without longitudinal posts and be configured to deform and adapt against the inner wall W of the main vessel under the load of the compressive force $F_C$ of the closure structure 110 in a manner wherein the resulting shape could be irregular and/or conform to the gaps G created between the closure structure 110 and the inner wall W, thus preventing gutters or leakage areas between the deployed prosthetic assembly 100 and the inner wall W within the proximal seal zone 123. For example, and not by way of limitation, strut heights, thicknesses, or other patterns may be varied (such as by laser cutting) around the circumference of the frame to achieve stiffer sections and more flexible sections such that the frame bends to the desired shape upon deformation by the exclusion structure 110.

Referring again to FIG. 4A, the circumferential struts 146 and/or longitudinal posts 147 may be arranged in a variety of geometrical patterns. In the examples shown in FIGS. 4A and 4C, the struts 146 are formed in a chevron or zig-zag configuration. One of ordinary skill will recognize that diamond-shaped patterns, sinusoidal configurations, closed cells, open cells, or other circumferentially expandable configurations are also possible. In some embodiments, the longitudinal posts 147 may be divided along their length into multiple, separated segments (not shown), e.g. where the struts 146 interconnect with the longitudinal posts 147. The plurality of struts 146 and posts 147 can be formed from a deformable material or from a resilient or shape memory material (e.g., nitinol). In other embodiments, the frame 141 can comprise a mesh or woven construction in addition to or in place of the circumferential struts 146 and/or longitudinal posts 147. For example, the frame may include a tube or braided mesh formed from a plurality of flexible wires or filaments arranged in a diamond pattern or other configuration. In another example, a metal tube may be laser cut to provide a desired strut and/or post geometry.

Figure 4B:
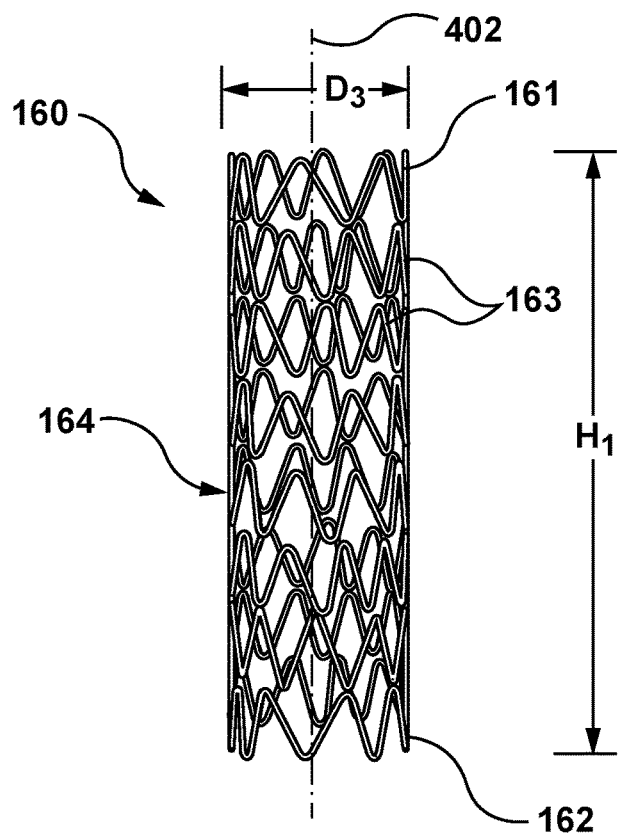
FIG. 4B is a side view of a support structure for use in a branch assembly and in accordance with an embodiment of the present technology.

FIG. 4B is a side view of a support structure 160, shown in a radially-expanded configuration, that can be used in embodiments of the branch assembly 130 shown in FIGS. 2A-2B and 4C-4E. Referring to FIGS. 2A-2B and 4B-4E together, an embodiment of the support structure 160 can be generally cylindrical having an upstream end 161 and a downstream end 162 formed around a longitudinal axis 402. The support structure 160 can have a circular or other suitable cross-sectional shape (e.g., oval, elliptical) configured to maintain patency of the proximal segment 134 of the branch assembly 130 (FIG. 2A) to provide blood flow therethrough. In some embodiments, the support structure 160 is a stent structure including a plurality of struts 163 forming an expandable inner skeleton or scaffold 164. The support structure 160 can provide such a scaffold 164 having radial rigidity to maintain patency of the proximal portion 142 of the outer branch prosthesis 140 to ensure that blood flow to the branch vessel BV is preserved when the branch assembly 130 is deployed alongside the exclusion structure 110 and subject to external radial pressure (FIGS. 2A-2B).

In some arrangements, the struts 163 may be circumferentially oriented and connected by a plurality of longitudinal ribs (not shown). The struts 163 can be arranged in a variety of geometrical patterns that can expand and provide sufficient resilience, buckling resistance, outward radial strength and/or column strength for maintaining the integrity of the support structure 160 and thereby the internal conduit 132 of the branch assembly 130 (e.g., through the proximal segment 134). For example, the struts 163 can be formed in a series of zig-zags and arranged in pairs 180 degrees out of phase with each other so as to form a series of diamonds. Alternative expandable geometries can include sinusoidal patterns, chevron configurations, closed cells, open cells, or other expandable configurations. In one embodiment, the support structure 160 can be a balloon expandable stent. However, in other embodiments, the support structure 160 can be a self-expanding stent provided that the support structure provides sufficient outward radial strength to maintain patency of the internal conduit 132 of the branch assembly 130.

Referring to FIG. 4B, the support structure 160 can have an entire longitudinal height $H_1$ that can be at least partially disposed with the first portion 142 of the outer branch prosthesis 140. In one embodiment, the height $H_1$ can be approximately 15 mm to about 80 mm. In particular embodiments the height $H_1$ can be about 30 mm or about 40 mm. When deployed, and seated within the first portion 142 of the outer branch prosthesis 140, a portion of the support structure 160 can be positioned outside of or upstream of the first portion 142. For example, the upstream end 161 of the support structure 160 can be positioned more upstream than the rim 153 of the outer branch prosthesis 140 by a distance $D_{U1}$ (FIG. 2A). In other embodiments, the upstream end 161 may be generally aligned with the rim 153 (FIGS. 4D-4E) or positioned downstream relative to the rim 153 (not shown).

The frame 141 of the outer branch prosthesis 140 and the support structure 160 may be made of different materials or, in some embodiments, the same material. In some embodiments, both the frame 141 and the support structure 160 include a resilient biocompatible metal, such as stainless steel, nickel cobalt or cobalt chromium alloys such as MP35N, or nickel titanium alloys such as nitinol. Superelastic shape memory materials such as nitinol can allow the device to be collapsed into a very low profile delivery configuration suitable for delivery through the vasculature via catheter, and allow self-expansion and/or balloon expansion to a deployed configuration suitably sized to cannulate a branch vessel BV. In some embodiments, the frame 141 and/or the support structure 160 can be laser cut from a single metal tube into their desired geometries, creating tubular scaffolds of interconnected struts. The frame 141 may then be shaped into a desired configuration, e.g. a flared, funnel-like or frustoconical shape within the first portion 142, using known shape-setting techniques for such materials. In a particular embodiment, the frame 141, and hence outer branch prosthesis 140, is self-expandable and the support structure 160 is balloon expandable. As explained above, in an embodiment, the support structure 160 may have a higher radial strength than the frame 141. The support structure 160 may have a higher radial strength than the frame 141 by using different materials, different sized structural elements (e.g. thicker or shorter struts), a different structural design, or other differences as would be contemplated by those skilled in the art.

While the outer branch prosthesis 140 includes the graft or sealing material 145 covering and/or lining an internal surface so as to prevent blood from leaking out of the internal conduit 132, the support structure 160 need not have occlusive properties. Accordingly, the scaffold 164 of the support structure 160 can be uncovered to, for example, allow free flow of blood collected within the inflow region 150 through the scaffold 164 and into the internal conduit 132 which is at least partially provided by the support structure 160. In other arrangements, the support structure 160 can be covered and/or lined with material. Such material may be permeable to blood, for example.

Figure 4C:
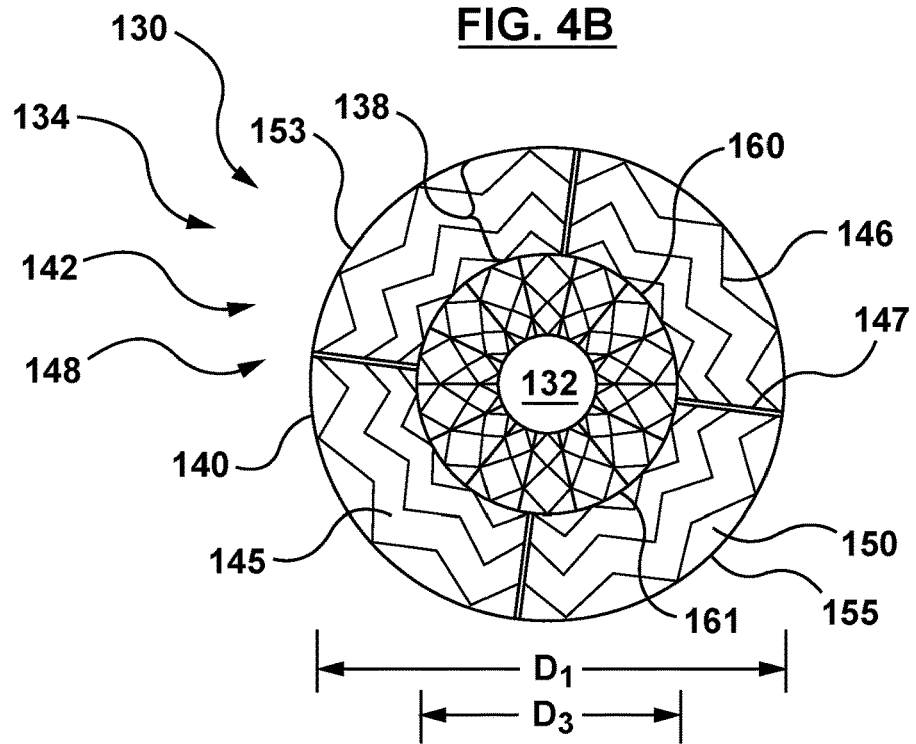
FIG. 4C is a top view of a branch assembly for use with the prosthetic assembly of FIG. 2A and in accordance with embodiments of the present technology.
Figure 4D:
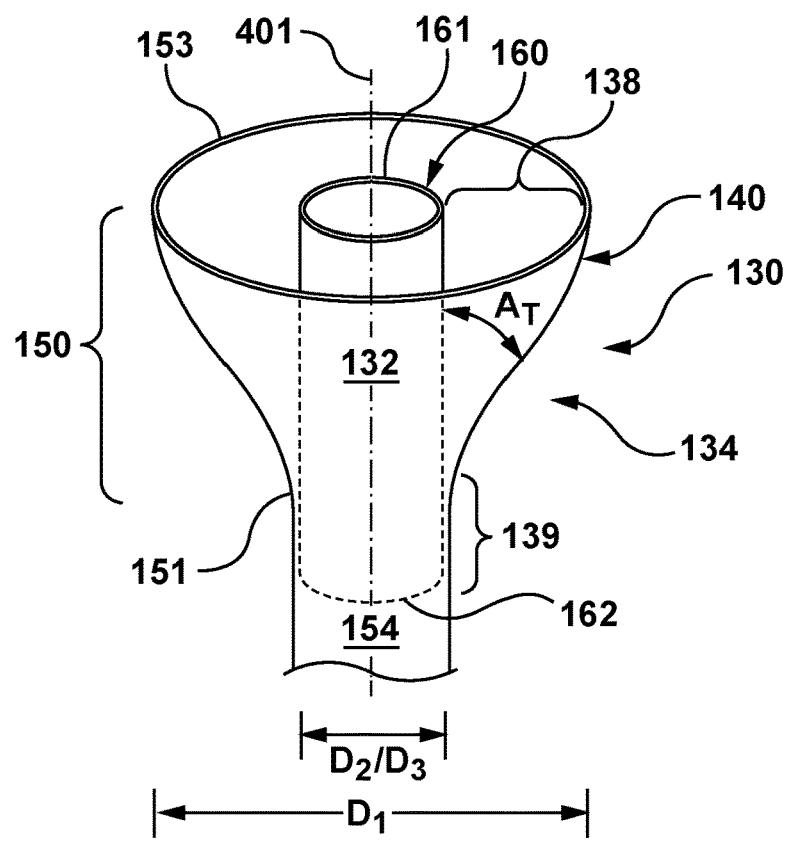
FIGS. 4D and 4E are schematic illustrations of a branch assembly for use with the prosthetic assembly of FIG. 2A and in accordance with embodiments of the present technology.

Referring to FIGS. 4C-4D, the support structure 160 is disposed within the outer branch prosthesis 140 with both in the radially expanded (unconstrained) configuration. It is noted that the support structure 160, in practice, may not be disposed within the outer branch prosthesis 140 with both in the radially expanded (unconstrained) configuration. As explained in more detail below, an embodiment of a method for deploying the prosthetic assembly 100 includes radially expanding the exclusion structure 110 prior to the outer branch prosthesis 140 and the support structure 160. However, FIGS. 4C-4D describe the support structure 160 disposed within the outer branch prosthesis 140 with both in the radially expanded (unconstrained) configuration such that the relative sizes of these two separate structures may be shown and described. Further, in other embodiments of the method described herein, the outer branch prosthesis 140 and/or the support structure 160 may be radially expanded prior to the exclusion structure 110. Accordingly, as shown in FIGS. 4C-4D, the first portion 142 of the outer branch prosthesis 140 can at least partially surround the support structure 160. In some embodiments, the downstream end 162 of the support structure 160 overlaps with a portion of the outer branch prosthesis 140 downstream of the inflow region 150 at an overlapping region 139, as shown in FIG. 4D. In the overlapping region, in some embodiments, the downstream end 162 of the support structure 160 can be coupled and/or compressively retained by the outer branch prosthesis 140. Thus, in various embodiments, the downstream end 162 of the support structure 160 has a cross-sectional dimension $D_3$ that is substantially the same as the cross-section dimension $D_2$ of the outer branch prosthesis 140 distal of the inflow region 150. In a particular embodiment, the overlapping region 139 may be approximately 5 mm to approximately 10 mm.

As further shown in FIGS. 4C-4D, the inflow region 150 of the outer branch prosthesis 140 has a larger cross-sectional dimension $D_1$ than the cross-sectional dimension $D_3$ of the support structure 160 with both in the radially expanded (unconstrained) configuration. This larger inflow region 150 and relative flexibility/radial strength of the inflow region 150 enables the inflow region 150 to engage and deform to the shape of the native tissue and the outer surface 127 of the exclusion structure 110 while the cross-sectional shape of the support structure 160 remains substantially undeformed or stable. As used herein, "substantially undeformed" can refer to situations in which the support structure 160 is not engaged or deformed, or to situations where the support structure is engaged but the radial strength of the support structure 160 resists deformation, or to situations in which the support structure 160 can deform slightly but the internal conduit 132 remains sufficiently open to preserve blood flow to the branch vessel BV.

As further shown in FIGS. 4C-4D, the cross-sectional dimension $D_1$ of the proximal end 152 of the inflow region 150 and defining the rim 153 is greater than the cross-sectional dimension $D_3$ of the upstream end 161 of the support structure 160. As such, the upstream end 161 of the support structure 160 is separated from the first portion 142 of the outer branch prosthesis 140 by a gap 138. Accordingly, in one embodiment and upon deployment, the substantially circular cross-sectional profile of the inflow region 150 of the first portion 142 can deform to a non-circular cross-sectional shape. As the support structure 160 is radially separated from the inflow region 150 of the outer branch prosthesis 140 by the gap 138, at least portions of the inflow region 150 can deform inwardly into the gap 138 without substantially deforming the support structure 160. In some embodiments, the frame 141 of the outer branch prosthesis 140 can be less rigid than the scaffold 164 of the support structure 160, allowing greater flexibility in the outer branch prosthesis 140 and/or more stability to the shape and position of the support structure 160. In some embodiments, the flexibility of the branch stent 140 enables the outer branch prosthesis 140 to absorb compressive forces (e.g., compressive force $F_C$ imparted by the radial expansion of the exclusion structure 110 and the inner wall W adjacent to the proximal segment 134 of the branch assembly 130) and enables the outer branch prosthesis 140 and the exclusion structure 110 to conform to each other component and to the inner wall W of the main vessel, encouraging tissue ingrowth and creating a seal to prevent leaks between or within the prosthetic assembly 100 and the native tissue. In some embodiments, the greater radial strength of the support structure 160 enables the support structure 160 to withstand the compressive force $F_C$ such as to maintain patency of the internal conduit 132.

Figure 4E:
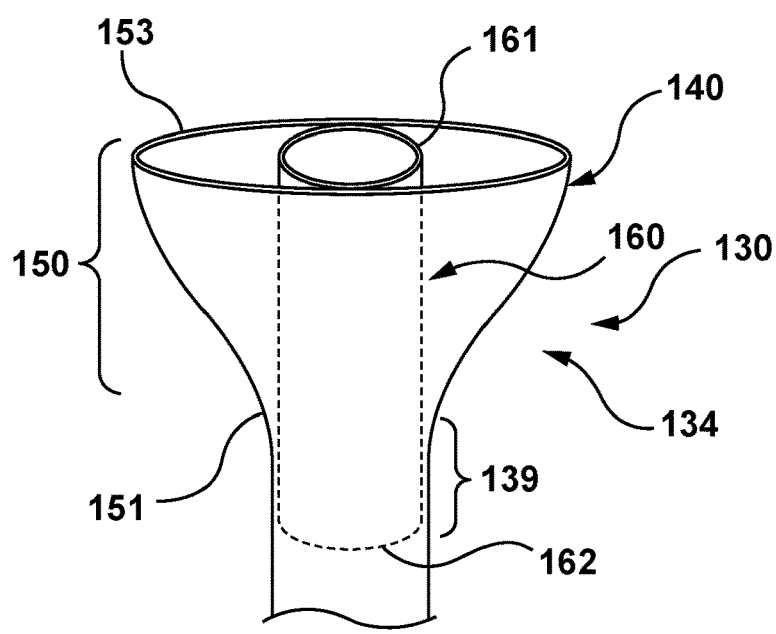

FIGS. 4D and 4E are schematic illustrations of embodiments of the proximal segment 134 of the branch assembly 130 in accordance with aspects of the present technology. FIG. 4D shows the branch assembly 130 in the radial expanded (unconstrained) configuration, as explained above, and FIG. 4E shows the branch assembly 130 in the deployed configuration with the compressive forces $F_C$ acting on the proximal segment 134 of the branch assembly 134. As shown in FIGS. 4D and 4E, the support structure 160 can be seated within the lumen 154 of the outer branch prosthesis 140 and within the first portion 142. The downstream end 162 of the support structure 160 may be anchored within the first portion 142, at the overlapping region 139, along a region of the first portion 142 distal to the inflow region 150.

Referring to FIGS. 4D and 4E together, the support structure 160 is disposed coaxially with the first portion 142 of the outer branch prosthesis 140 along the central longitudinal axis 402. As illustrated, the support structure 160 can be oriented along the central longitudinal axis 402, and the inflow region 150 of the outer branch prosthesis 140 can flare outward from the longitudinal axis 402 by a taper angle $A_T$. In some embodiments, the frame 141 of the inflow region 150 may generally curve outward from the transition 151 to the proximal end 152 (rather than linear), the taper angle $A_T$ can continuously change between the transition 151 and the proximal end 152. In some embodiments, the taper angle $A_T$ may be consistent along the inflow region 150 between the transition 151 and the proximal end 152. In some arrangements, the taper angle $A_T$ can be the same around the circumference 155 of the proximal end 152 of the outer branch prosthesis 140; however, in other embodiments, the taper angle $A_T$ can vary around the circumference 155. In some embodiments, the taper angle $A_T$ can be approximately 30° to about 75°, and in other embodiments, between approximately 40° and about 60°.

FIG. 4E shows an embodiment of the proximal segment 134 of the branch stent assembly 130 in the deployed configuration (i.e., with compressive forces $F_C$ acting on it) without showing the exclusion structure 110 or the inner wall W of the main vessel. As can be seen in FIG. 4E (similar to FIG. 2B), the compressive forces $F_C$ acting on the outer branch prosthesis 140 causes at least the inflow region 150 of the outer branch prosthesis 140 between the inner wall W and the closure structure 110 to deform (e.g., to a non-circular or non-symmetrical cross-sectional shape, an oval cross-sectional shape, elliptical cross-sectional shape, an eye-shaped cross-section, etc.), while the support structure 160 remains substantially undeformed. The support structure 160 can be configured to substantially maintain patency of blood flow through the proximal segment 134 even when exposed to the compressive forces $F_C$ through the outer branch prosthesis 140. Thus, the support structure 160 can maintain a circular or other desirable cross-section to maintain sufficient blood flow through the branch assembly 130.

Figure 5A:
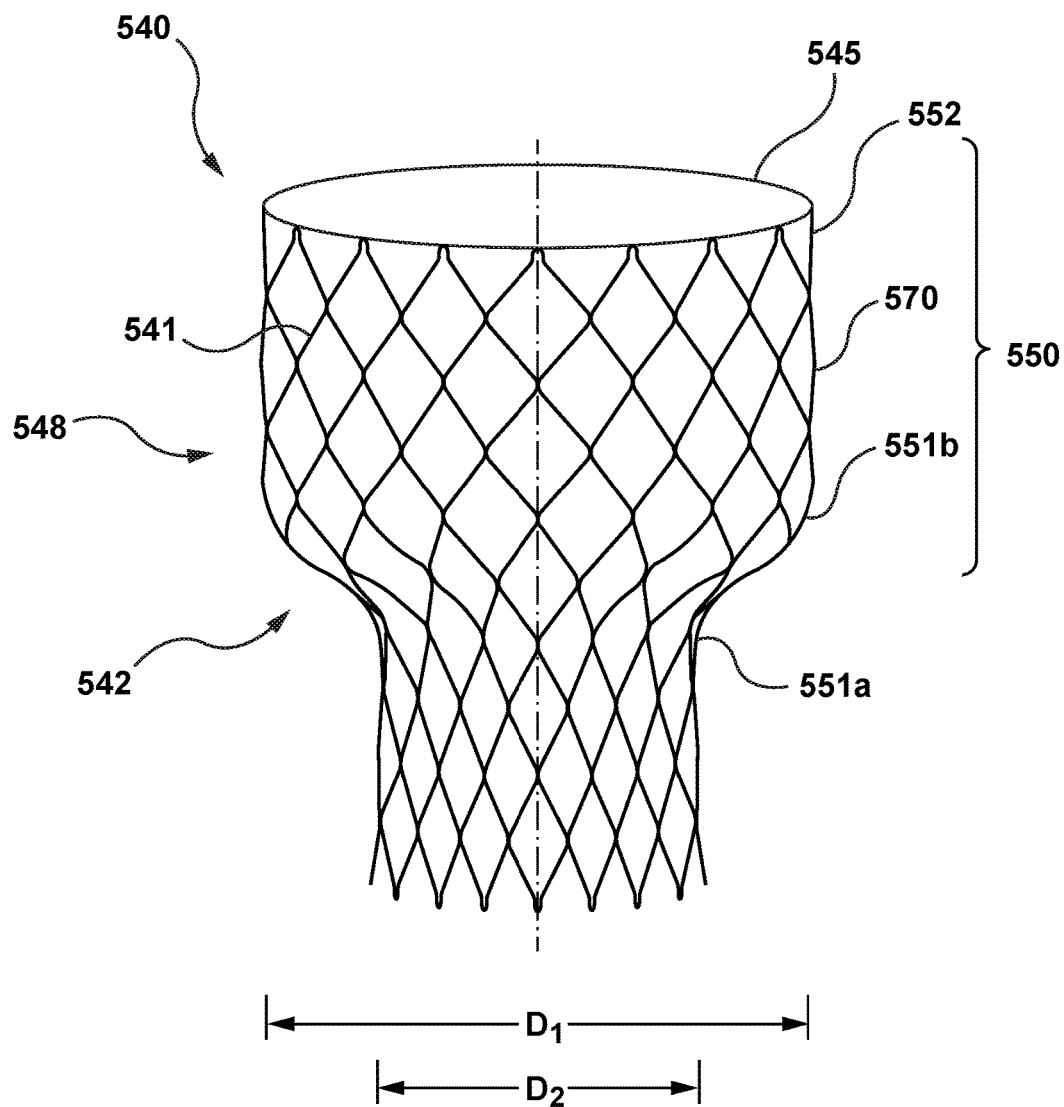
FIG. 5A a side view of a self-expanding outer branch prosthesis having a vertical portion at an inflow region for engaging the aortic wall and the exclusion structure in accordance with another embodiment of the present technology.
Figure 5B:
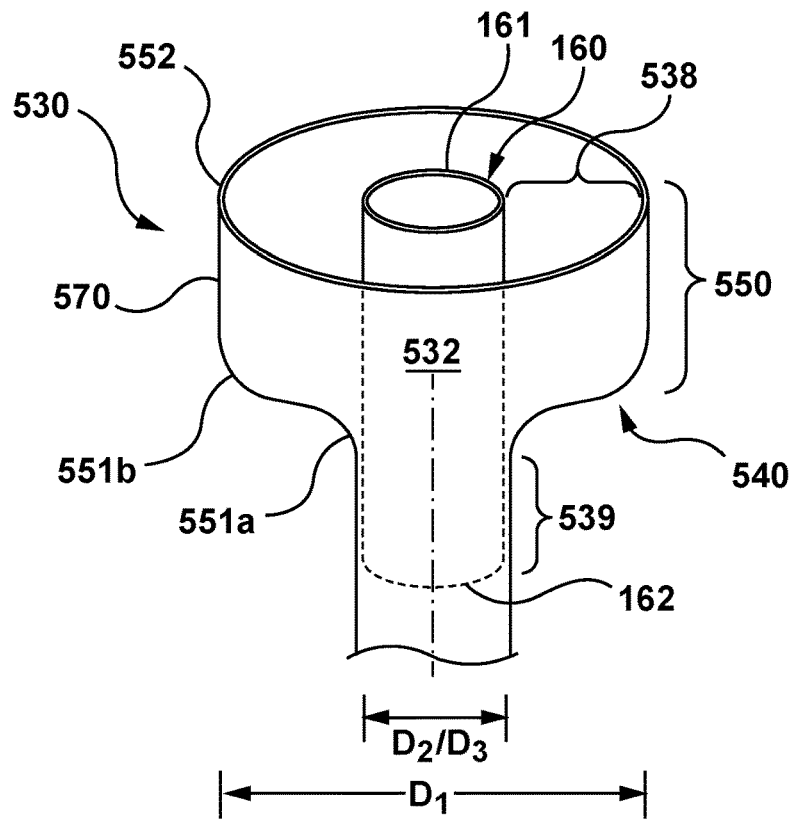
FIGS. 5B-5C are schematic illustrations of a branch assembly incorporating the self-expanding outer branch prosthesis of FIG. 5A and in accordance with an embodiment of the present technology.
Figure 5C:
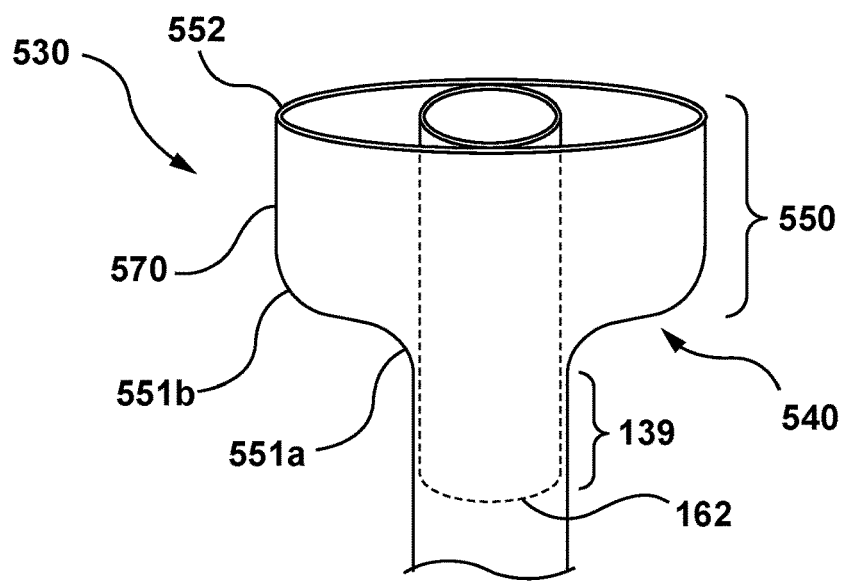

FIG. 5A is a side view of an upstream portion 548 of an outer branch prosthesis 540, shown in the radially-expanded (unconstrained) configuration, and in accordance with another embodiment of the present technology. FIGS. 5B and 5C are schematic illustrations of a branch assembly 530 incorporating the outer branch prosthesis 540 of the FIG. 5A and the support structure 160. FIG. 5B shows the branch assembly 530 in the radially expanded (unconstrained) configuration and FIG. 5B shows the branch assembly 530 in the deployed configuration with the compressive forces $F_C$ acting on the proximal segment 534 of the branch assembly 530. The branch assembly 530 includes features generally similar to the features of the branch assembly 130 described above with reference to FIGS. 4C-4E. For example, the branch assembly 530 includes the support structure 160 configured to maintain the patency of the branch stent assembly 530, and an outer branch prosthesis 540 at least partially encompassing the support structure 160 within the first portion 542. However, in the embodiment shown in FIGS. 5A-5C, the inflow region 550 of the outer branch prosthesis includes a vertical segment 570 for engaging the inner wall W of the main vessel and the exclusion structure 110 within the proximal seal zone 123 (FIGS. 2A and 2B).

Referring to FIGS. 5A-5C together, the first portion 542 of the outer branch prosthesis 540 can include the inflow region 550 having a first transition 551a and a second transition 551b between which the cross-sectional dimension of the outer branch prosthesis 540 transitions from the second cross-sectional dimension $D_2$ to the first cross-sectional dimension $D_1$. Following the second transition 551b, the inflow region 550 includes the vertical segment 570 which spans between the second transition 551b and the proximal end 552. The vertical segment 570 is configured to press outwardly against the inner wall W of the main vessel, the exclusion structure 110 when deployed, and is deformable to further press outwardly into the gaps G created between the exclusion structure 110 and the inner wall W where the branch assembly 530 is deployed in parallel. Similar to the branch assembly 130 illustrated in FIGS. 4C-4E, the support structure 160 is disposed within the outer branch prosthesis 540. The support structure has a cross-sectional dimension $D_3$ that is less than that the cross-sectional dimension $D_1$ of the inflow region 550 with the branch assembly 530 in the radially expanded configuration, thereby providing a gap 538 between at least the vertical segment 570 of the inflow region 550 and the support structure 160, as shown in FIG. 5B. Upon deployment, deformation of the inflow region 550 can occur while the support structure 160 maintains patency of the internal conduit 532, as shown in FIG. 5C. Accordingly, the inflow region 550 is configured to conform to the oval, elliptical, eye-shaped, or irregularly shaped region created by deploying side-by-side stent-grafts, and thereby preventing blood from leaking through regions exterior to the lumen 114 of the exclusion structure 110 (FIGS. 2A and 2B) and an internal conduit 532 provided by the branch assembly 530 (FIGS. 5B and 5C). By preventing such leakage, the prosthetic assembly 100 can avoid or inhibit fluid pressurization of the distally located tissue defect (e.g., aneurysm).

Figure 1F:
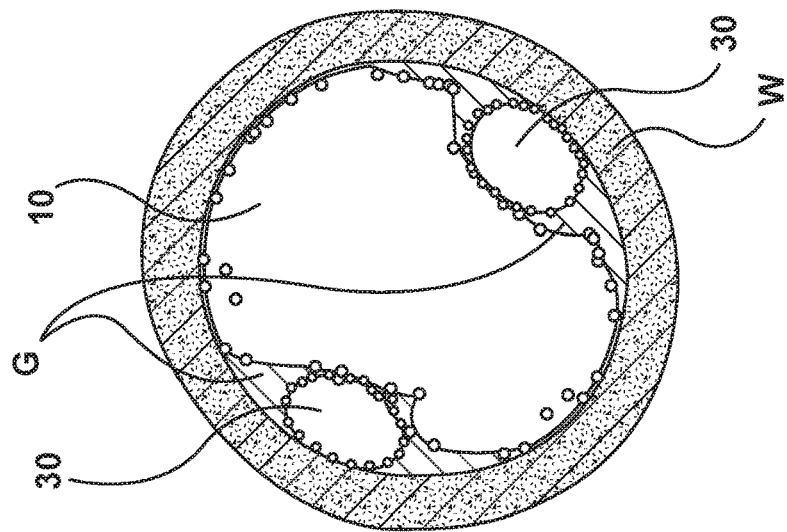
FIGS. 1D-1F are schematic illustrations of chimney endovascular aortic repair techniques at an abdominal aortic aneurysm that may result in undesirable gutters.
Figure 1E:
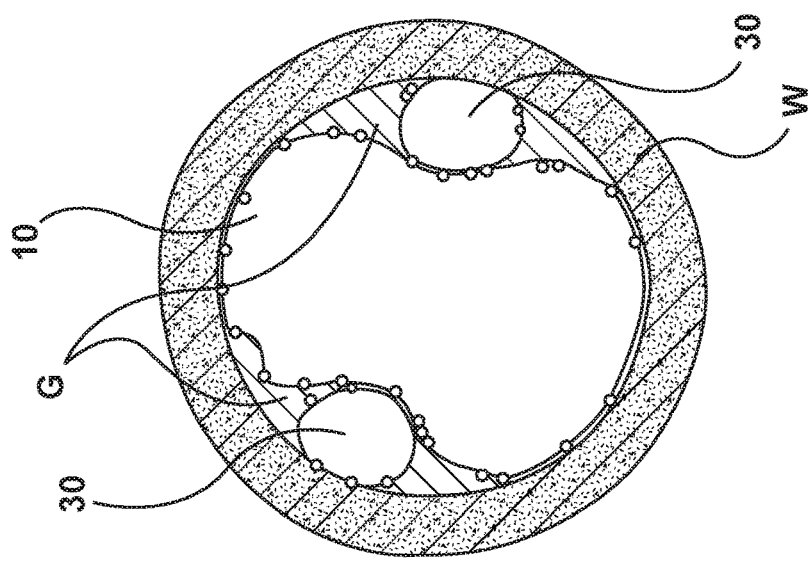
Figure 1D:
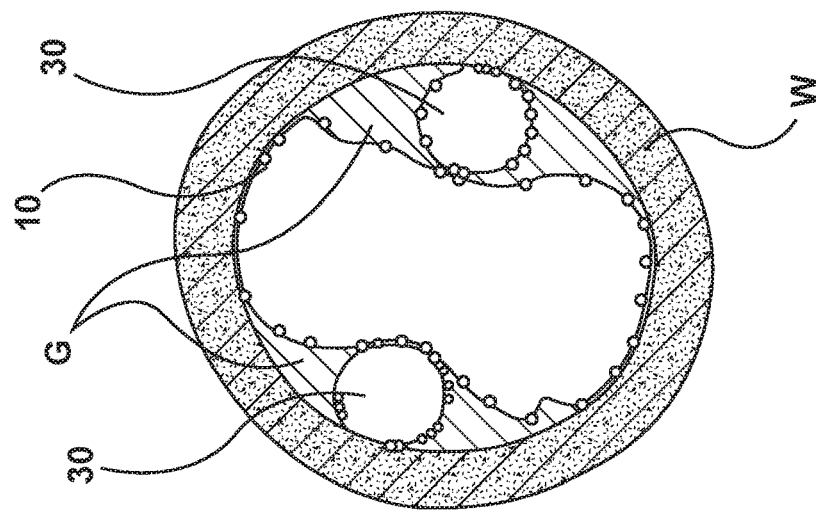
Figure 6:
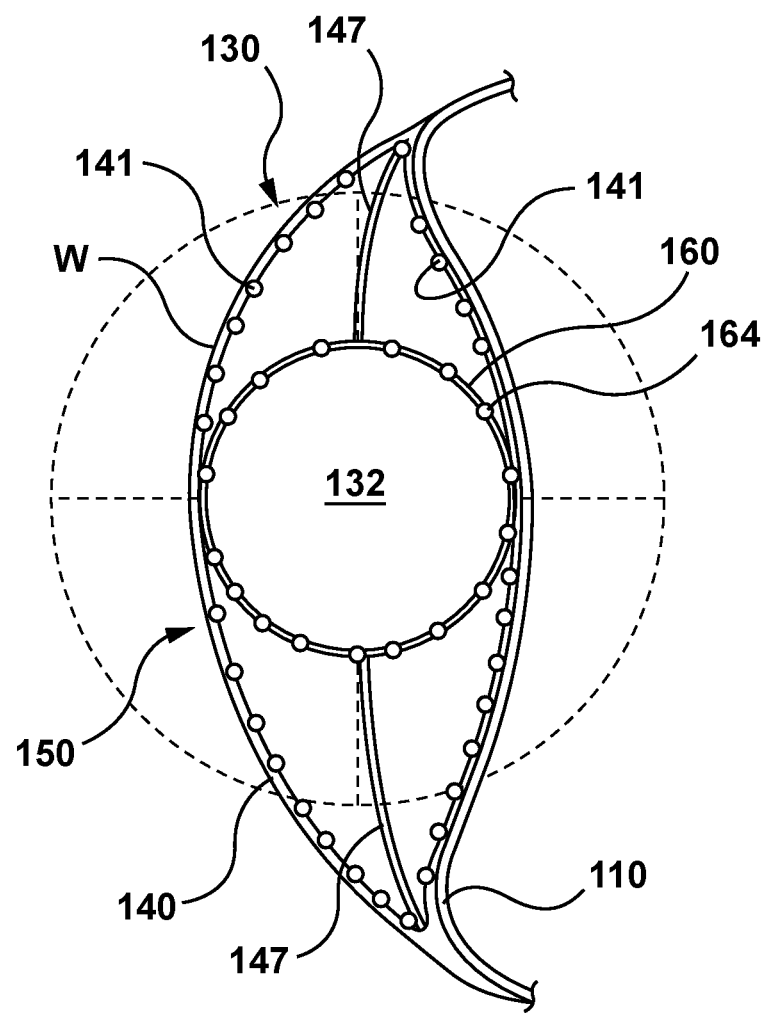
FIG. 6 is a schematic top view of a branch assembly in a radially-expanded configuration and in a deployed configuration in accordance with an embodiment of the present technology.

As explained above in the Background section, some conventional "snorkel" or chimney stent-grafts deployed with an main vessel endoprosthesis result in gaps or gutters G (see FIGS. 1D-1F) or may not provide sufficient blood flow to the branch vessel (FIG. 1F). The present technology provides prosthetic assemblies 100 having branch assemblies 130 that inhibit blood leakage through the gaps while preserving a blood flow conduit to supply the branch vessels. In particular, FIG. 6 shows a top view that illustrates how flexibility and/or deformation of the frame 141 at the inflow region 150 allows the outer branch prosthesis 140 to distort relative to the radially-expanded configuration, as shown by the dashed lines, into a deployed configuration, as shown by the bolded lines. As shown in FIG. 6, the outer branch prosthesis 140, when deployed or implanted adjacent the exclusion structure 110 at the proximal region 102 of the prosthetic assembly 100 within the main vessel, can conform to the irregular shaped space created between the closure structure 110 and the inner wall W of the main vessel on either side of the branch assembly 130. As discussed above, the frame 141 may include features, such as the longitudinal posts 147, to orient the outer branch prosthesis 140 to the shape shown in FIG. 6. Alternatively or in addition to, the flexibility of the frame 141 and the outer branch prosthesis 140 enables the outer branch prosthesis 140 to bend, twist, and/or stretch such that the overall shape of the outer branch prosthesis 140 has a deployed configuration that conforms to the inner wall W and the exclusion structure 110 (e.g., a generally more oval or elliptical, eye-shaped, or other irregular shape). As the outer branch prosthesis 140 is deformed into the shape shown in FIG. 6, the support structure 160 maintains its shape (i.e., is substantially undeformed), thereby maintaining patency of the internal conduit 132 and assuring sufficient blow flow to the branch vessel. Referring to FIG. 6 as compared to FIGS. 1D-1F, the outer branch prosthesis 140 substantially covers the gaps G in the deployed configuration. The outer branch prosthesis 140 could also be pre-shaped to be in a generally oval or elliptical, or other shape, when in an unbiased condition.

Several suitable delivery and deployment methods are discussed herein and discussed further below; however, one of ordinary skill in the art will recognize a plurality of methods suitable to deliver the prosthetic assembly 100 to the target vessel region $T_R$ (e.g., percutaneous, transcatheter delivery, for example, using a femoral artery approach). Additionally, one of ordinary skill in the art will recognize a plurality of methods suitable to deploy the prosthetic assemblies 100 from a compressed configuration for delivery to the deployed configuration illustrated in FIGS. 2A and 2B.

Figure 7:
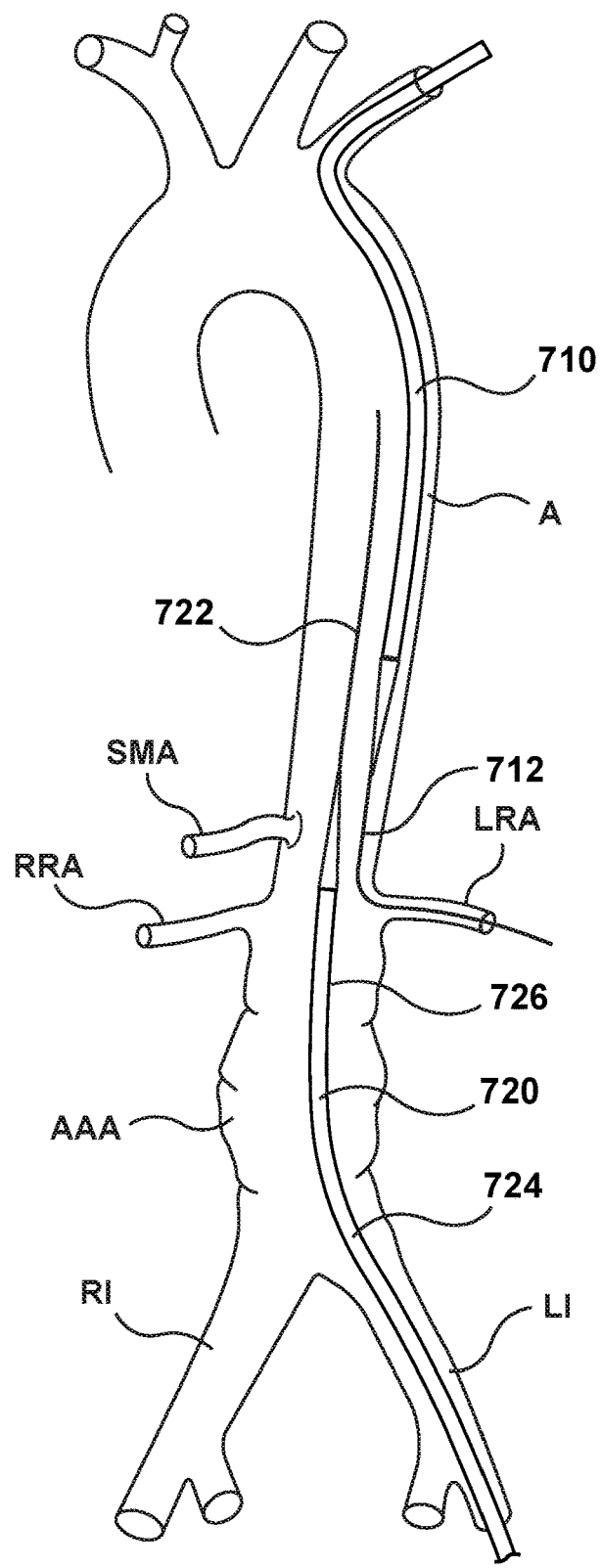
FIG. 7 schematically shows a step of a method of delivering the prosthetic assembly of FIG. 2A to a target site in the abdominal aorta in accordance with an embodiment of the present technology.

FIG. 7 shows a delivery system 700 for delivering and deploying the prosthetic assembly 100 in the abdominal aorta for the repair of an abdominal aortic aneurysm AAA in accordance with an embodiment of the present technology. The delivery system 700 can include a first delivery catheter 710 configured for delivery and deployment of a branch assembly 130 radially-compressed therein. The first delivery catheter 710, advances over a guidewire 712 and to a target branch vessel (e.g., LRA, RRA and SMA) within the target vessel region (e.g., within or proximal to the AAA) target vessel region. The guidewire 712 is typically inserted into the left brachial artery (not shown) and into the descending aorta A, as is well known in the art.

Figure 8A:
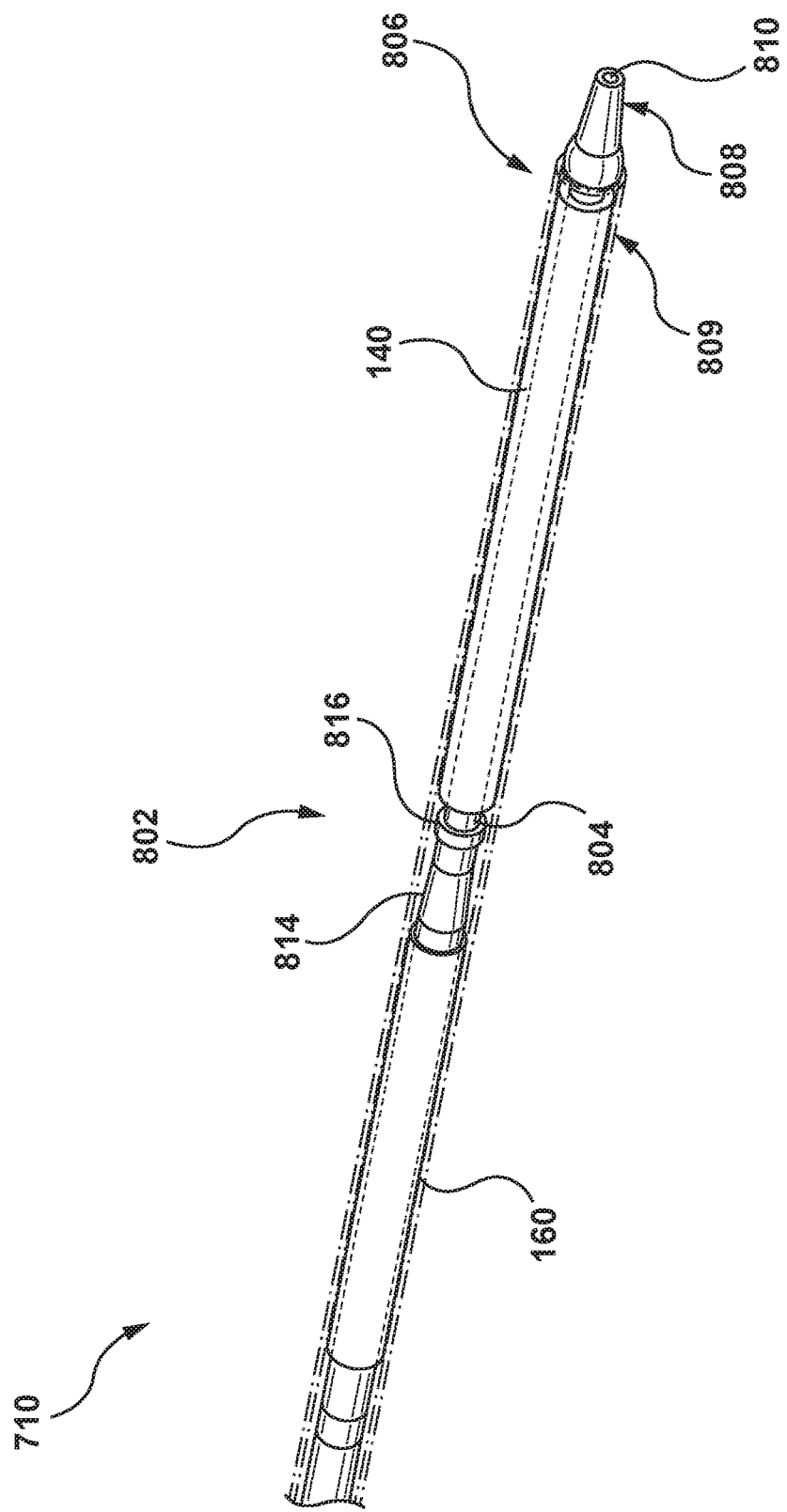
FIG. 8A is side partial cut-away view of a distal portion of a delivery system in accordance with an embodiment of the present technology.
Figure 8B:
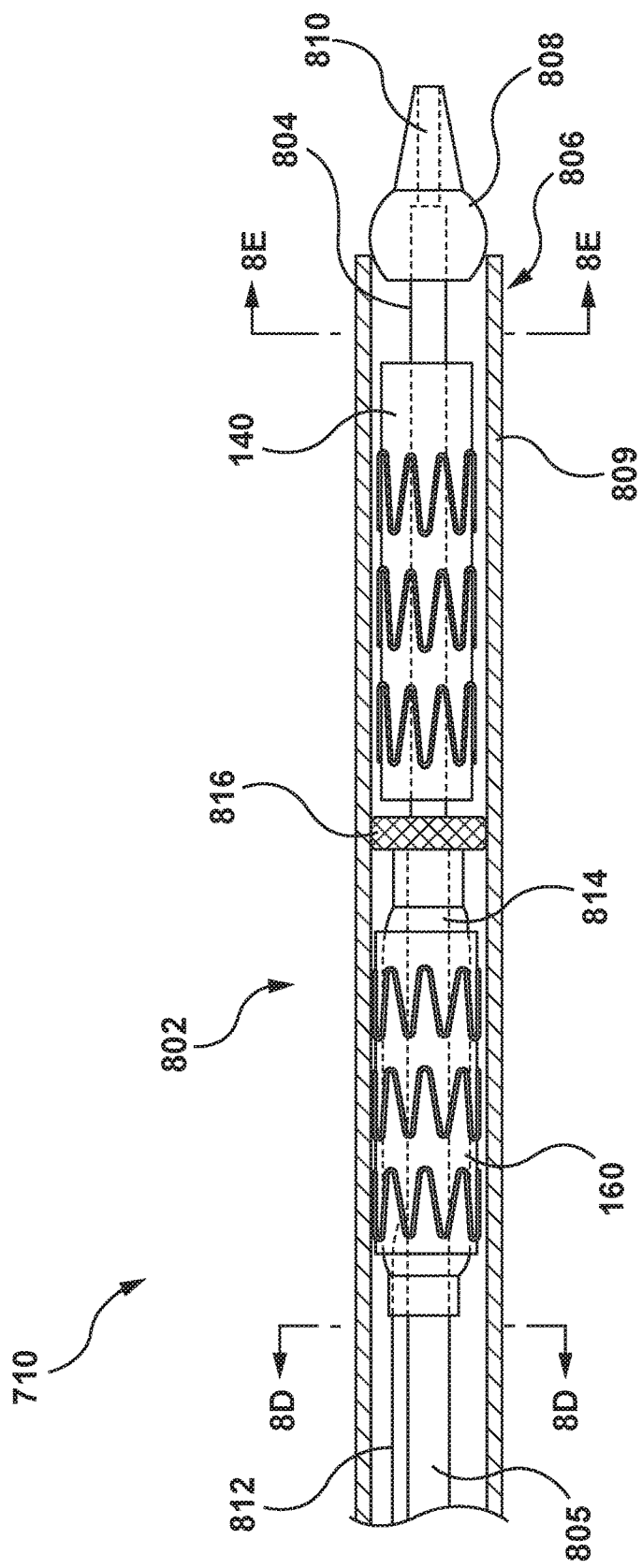
FIG. 8B is an enlarged sectional view of the distal portion of the delivery system shown in FIG. 8A and in accordance with an embodiment of the present technology.
Figure 8C:
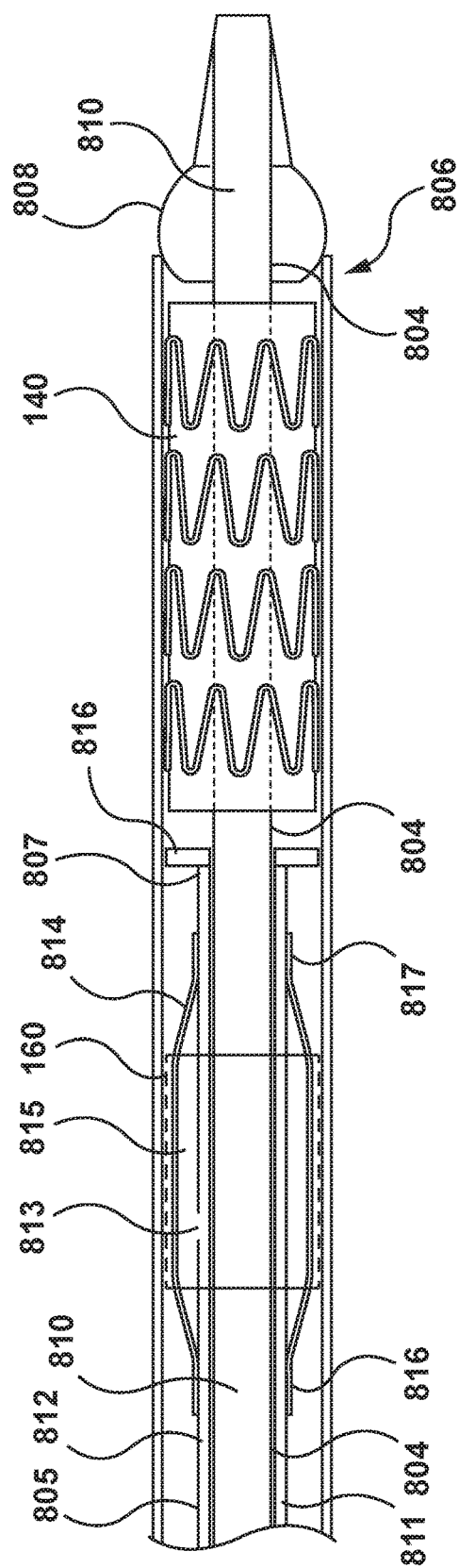
FIG. 8C is a schematic longitudinal cross-section of the distal portion of the delivery system shown in FIG. 8A and in accordance with an embodiment of the present technology.

FIG. 8A is side partial cut-away view of a distal portion 802 of the first delivery catheter 710 and FIG. 8B is an enlarged longitudinal schematic of the distal portion 802 of the first delivery catheter 710 shown in FIG. 8A in accordance with an embodiment of the present technology. FIG. 8C is a schematic longitudinal cross-section of the distal portion 802. Referring to FIGS. 8A-8C, the distal portion 802 of the first delivery catheter 710 houses the outer branch prosthesis 140 and the support structure 160 within a sheath 809 for simultaneous delivery and sequential deployment.

Figure 8E:
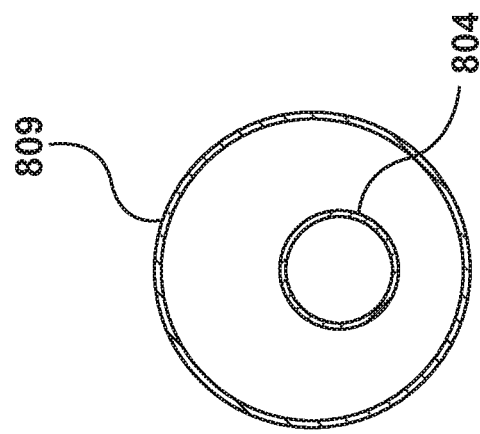
FIG. 8E is a cross-section taken along line 8E-8E of FIG. 8C.
Figure 8D:
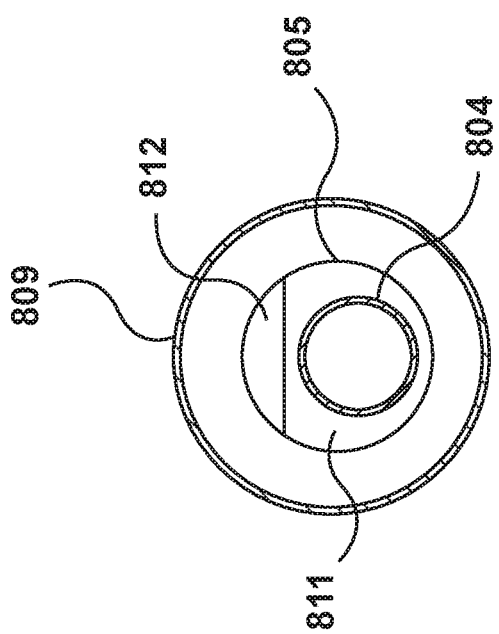
FIG. 8D is a cross-section taken along line 8D-8D of FIG. 8C.

The first delivery catheter 710 includes a shaft 805 including a guidewire lumen 811 and an inflation lumen 812 extending from a handle (not shown) at a proximal end of the first delivery catheter 710 outside the body. As shown in FIG. 8D, the shaft 805 is a bi-lumen construction. Those skilled in the art would understand that other constructions may be utilized. A distal end 807 of the shaft 805 terminates distal of the support structure 160 and proximal of the outer branch prosthesis 140. The distal end 807 of the shaft 805 may include a stent stop 816 to prevent the outer branch prosthesis 140 from moving proximally with the sheath 809 when the sheath 809 is retracted to enable the outer branch prosthesis to expand, as known to those skilled in the art.

As shown in FIGS. 8A-8C, a balloon 814 is attached to the shaft 805. In particular, a proximal neck of the balloon 814 is attached to the shaft 805 at a proximal connection 816 and a distal neck of the balloon 814 is attached to the shaft 805 at a distal connection 817. The shaft 805 includes an opening 813 which is disposed within an interior 815 of the balloon 814 and is in communication with the inflation lumen 812. Thus, when it is desired to inflate the balloon 814, an inflation fluid is injected into the inflation lumen 812 from an inflation source (not shown). The inflation fluid exits the inflation lumen 812 through the opening 813 and into the interior 815 of the balloon 814, thereby inflating the balloon 814. The support structure 160 is crimped onto the balloon 814 and within the sheath 809 for delivery.

As shown in FIGS. 8C and 8D, an inner member 804 extends through the guidewire lumen 811 of the shaft 805. The inner member 804 is slidably disposed through the guidewire lumen 811 of the shaft 805 such that the inner member 804 and the shaft 805 may slide longitudinally relative to each other. The inner member 804 extends along the length of the delivery catheter 710 and is accessible by a handle (not shown) outside the body. Further, the inner member 804 extends distally beyond the distal end 807 of the shaft 805, as shown in FIG. 8C. The self-expanding outer branch prosthesis 140 is radially-contracted at a distal end 806 of the inner member 804 adjacent to a delivery catheter tip 808 and is maintained in the low-profile, radially-contracted configuration by the delivery sheath 809. The delivery sheath 809 is configured to be retracted proximally for deployment of the self-expanding outer branch prosthesis 140 within the target branch vessel and/or the main vessel. The inner member 804 may in one embodiment be a braided tube that can tolerate deployment as well as retrieval forces. For example, as explained in more detail below, once the outer branch prosthesis 140 is delivered to and deployed within the target branch vessel by retraction of the delivery sheath 809, the inner member 804 may be retracted proximally such that the first delivery catheter 710 can be advanced distally for placement of the support structure 160 without risk of advancing the first delivery catheter 710 too far distally in the branch vessel. The inner member 804 also has a guidewire lumen 810 that runs coaxially along a full length of the inner member 804 and which is configured to receive the guidewire 712 (FIG. 7) there-through.

Figure 9A:
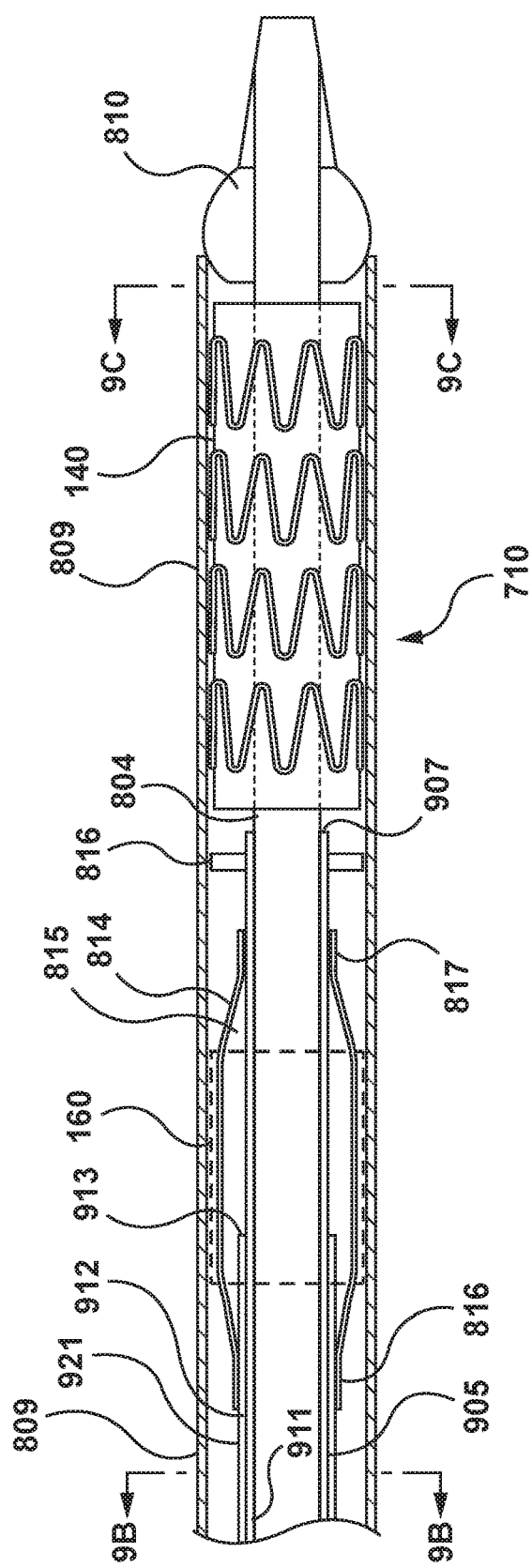
FIG. 9A is a schematic longitudinal cross-section of the distal portion of a delivery system similar to that shown in FIG. 8A and in accordance with an embodiment of the present technology.
Figure 9C:
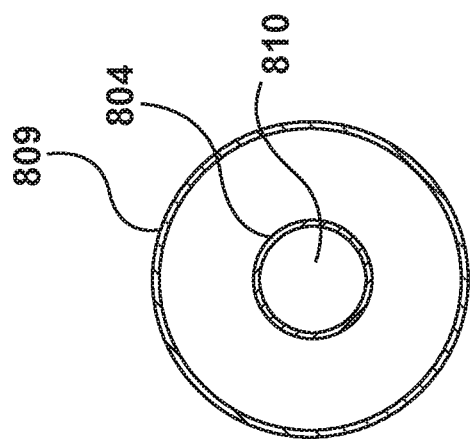
FIG. 9C is a cross-section taken along line 9C-9C of FIG. 9A.
Figure 9B:
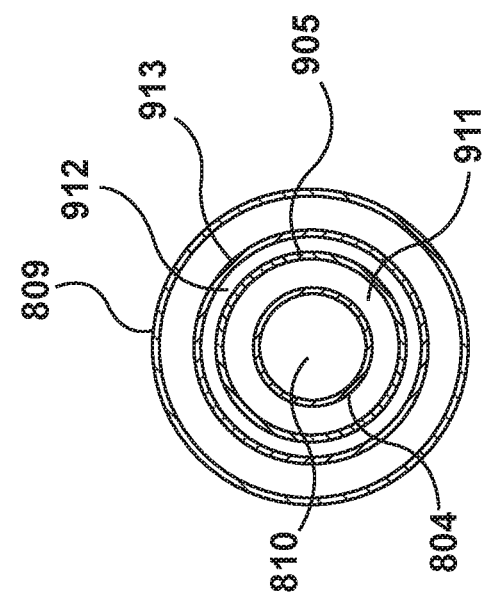
FIG. 9B is a cross-section taken along line 9B-9B of FIG. 9A.

In an alternative arrangement, the inner member 804 and other shafts of the first delivery catheter 710 may be arranged in a co-axial relationship, as shown in FIGS. 9A-9C. The reference numerals for parts that are not changed from FIGS. 8C-8E are carried forward from FIGS. 8C-8E. FIG. 9A is a schematic longitudinal cross-section of the distal portion 802 of the first delivery shaft 710. FIGS. 9B and 9C are schematic cross-sections taken at lines 9B and 9C of FIG. 9A, respectively. The distal portion 802 houses the outer branch prosthesis 140 and the support structure 160 within the delivery sheath 809 for simultaneous delivery and sequential deployment.

The first delivery catheter 710 includes an inflation shaft 921, a guidewire shaft 905 disposed through a lumen of the inflation shaft 921, and the inner member 804 disposed through a guidewire lumen 911 of the guidewire shaft 905. An inflation lumen 912 is disposed between an outer surface of the guidewire shaft 905 and an inner surface of the inflation shaft 921. The inflation shaft 921 extends from a proximal end of the first delivery catheter 710 to a location within the interior 815 of the balloon 814. The guidewire shaft 905 extends from a handle (not shown) at a proximal end of the first delivery catheter 710 to a distal end 907 terminating distal of the support structure 160 and proximal of the outer branch prosthesis 140. The distal end 907 of the guidewire shaft 905 may include the stent stop 816 to prevent the outer branch prosthesis 140 from moving proximally with the sheath 809 when the sheath 809 is retracted to enable the outer branch prosthesis 140 to expand, as known to those skilled in the art.

As shown in FIG. 9A, a proximal neck of the balloon 814 is attached to the inflation shaft 921 at a proximal connection 816 and a distal neck of the balloon 814 is attached to the guidewire shaft 905 at a distal connection 817. The proximal and distal necks of the balloon 814 are attached to different shafts because the inflation shaft 921 terminates within the interior 815 of the balloon 814, as described above. However, other configurations of the shafts 921/805 may also be used. Thus, when it is desired to inflate the balloon 814, an inflation fluid is injected into the inflation lumen 912 from an inflation source (not shown). The inflation fluid exits the inflation lumen 912 through a distal opening 913 of the inflation shaft 921 and into the interior 815 of the balloon 814, thereby inflating the balloon 814. The support structure 160 is crimped onto the balloon 814 and within the sheath 809 for delivery.

As shown in FIG. 9A, the inner member 804 extends through the guidewire lumen 911 of the guidewire shaft 905. The inner member 804 is slidably disposed through the guidewire lumen 911 of the guidewire shaft 905 such that the inner member 804 and the guidewire shaft 905 may slide longitudinally relative to each other. The inner member 804 extends along the length of the delivery catheter 710 and is accessible by a handle (not shown) outside the body. Further, the inner member 804 extends distally beyond the distal end 907 of the guidewire shaft 905, as shown in FIG. 9A. The self-expanding outer branch prosthesis 140 is radially-contracted at the distal end 806 of the inner member 804 adjacent to the delivery catheter tip 808 and is maintained in the low-profile, radially-contracted configuration by the delivery sheath 809. The delivery sheath 809 is configured to be retracted proximally for deployment of the self-expanding outer branch prosthesis 140 within the target branch vessel and/or the main vessel. The inner member 804 may in one embodiment be a braided tube that can tolerate deployment as well as retrieval forces. For example, as explained in more detail below, once the outer branch prosthesis 140 is delivered to and deployed within the target branch vessel by retraction of the delivery sheath 809, the inner member 804 may be retracted proximally such that the first delivery catheter 710 can be advanced distally for placement of the support structure 160 without risk of advancing the first delivery catheter 710 too far distally in the branch vessel. The inner member 804 also has a guidewire lumen 810 that runs coaxially along a full length of the inner member 804 and which is configured to receive the guidewire 712 (FIG. 7) there-through.

Those skilled in the art would understand that although the shafts described in FIGS. 8A-8E and 9A-9C were described as extending the length of the delivery catheter, some or all of the shafts may be arranged in a rapid exchange manner, where appropriate, as known by those skilled in the art.

Referring back to FIG. 7, the delivery system 700 also includes a second delivery catheter 720 carrying the exclusion structure 110 (e.g., a main vessel stent-graft) compressed therein. The second delivery catheter 720 is advanced over a main vessel guide wire 722 and to the target vessel region in the abdominal aorta A. The guide wire 722 is typically inserted into the femoral artery (not shown) and percutaneously routed upstream through the left iliac artery LI to abdominal aorta, as is known in the art. Delivery of the second delivery catheter 720 can also occur through right iliac artery RI. The location of the first and/or second delivery catheters 710, 720 and/or the branch assembly 130 and/or exclusion structure 110 may be verified radiographically when delivery system and/or prosthetic assembly components include radiopaque markers, as is known in the art. For example, in one embodiment, the first and/or second ends 121, 125 of the closure structure 110 may include radiopaque markers to aid in positioning. The exclusion structure 110 is mounted on a catheter shaft 724 of the second delivery catheter 720 and an outer delivery sheath 726 of the second delivery catheter 720 covers and restrains the exclusion structure 110 in a compressed configuration for delivery thereof.

Figure 10:
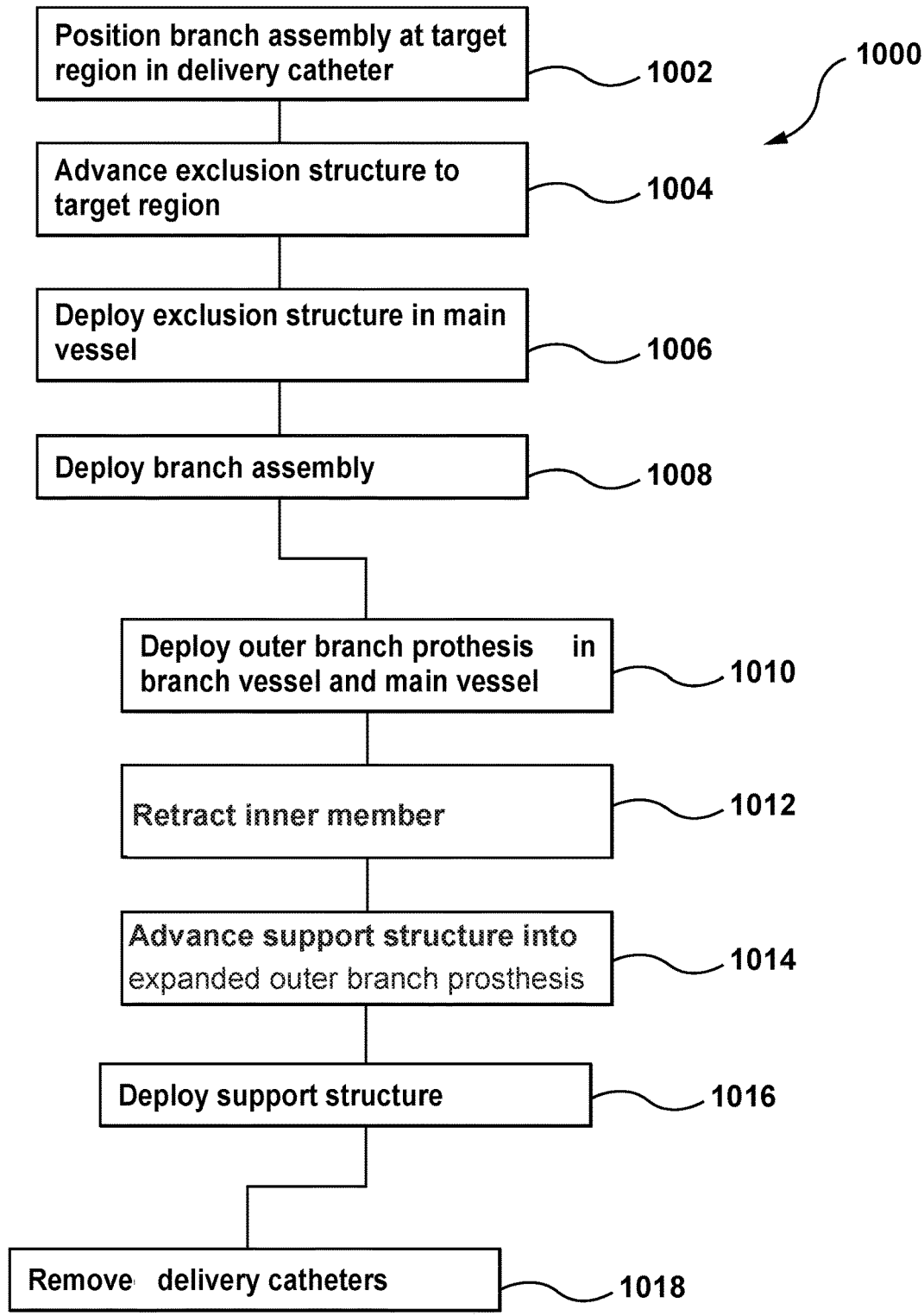
FIG. 10 is flow diagram illustrating a method for repairing a target tissue defect in a blood vessel of a patient in accordance with an embodiment of the present technology.

FIG. 10 is block diagram illustrating a method 1000 for repairing a target tissue defect in a blood vessel of a patient with the prosthetic assembly 100 described above with reference to FIGS. 2A-9C and in accordance with an embodiment of the present technology. FIGS. 11A-11G show schematically some of steps of the method of FIG. 10. The method of FIG. 10 and FIGS. 11A-11G show only one branch assembly 130 being delivered and deployed to the right renal artery RRA. Those skilled in the art would recognize that the method could include a second branch assembly 130 being delivered and deployed to the left renal artery LRA or other branch vessels at a target site. Accordingly, the description of the method 1000 describing the delivery of a single branch assembly 130 is non-limiting.

Figure 11A:
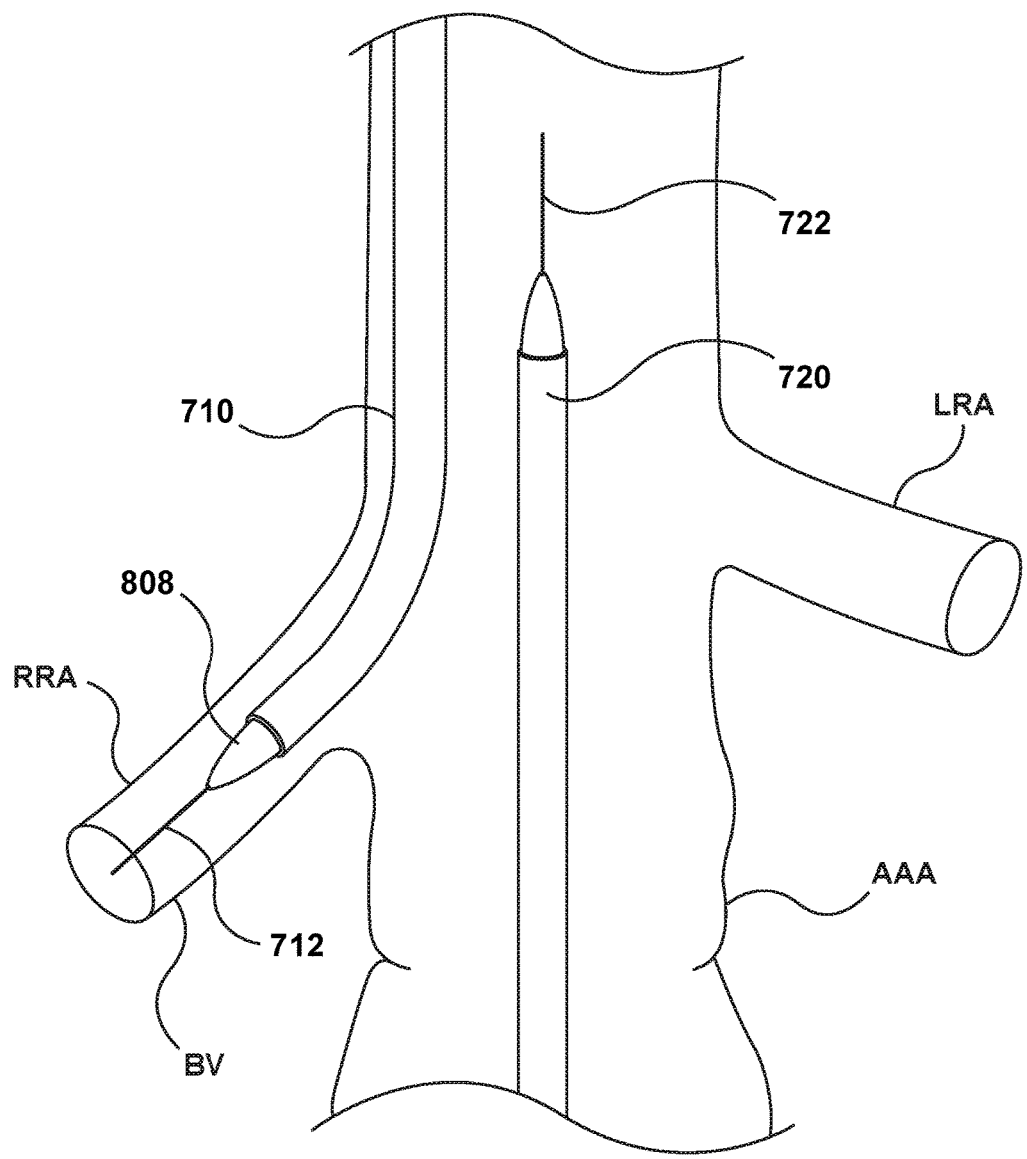
FIGS. 11A-11G are schematic illustrations showing various steps in the method of FIG. 10.

Referring to FIG. 10, the method 1000 can include positioning the first delivery catheter 710 having the branch assembly 130 disposed therein in a radially-contracted configuration to a region of the blood vessel having the target tissue defect (block 1002). In this step, the distal tip 808 of the first delivery catheter 710 is preferably disposed within a branch vessel BV and a portion of the first delivery catheter housing the first portion 142 of the outer branch assembly 140 is preferably disposed in the main vessel. The first delivery catheter 710 may be advanced to the location over the guidewire 712. FIG. 11A schematically shows step 1002.

The method 1000 can also include a step advancing the second delivery catheter 712 having an exclusion structure (e.g. main stent-graft) over the second guidewire 722 to the location of the target tissue defect (block 1004). In this step, a distal tip of the second delivery catheter is advanced to a location upstream of the target tissue defect (e.g. upstream of the aneurysm AAA).

Figure 11B:
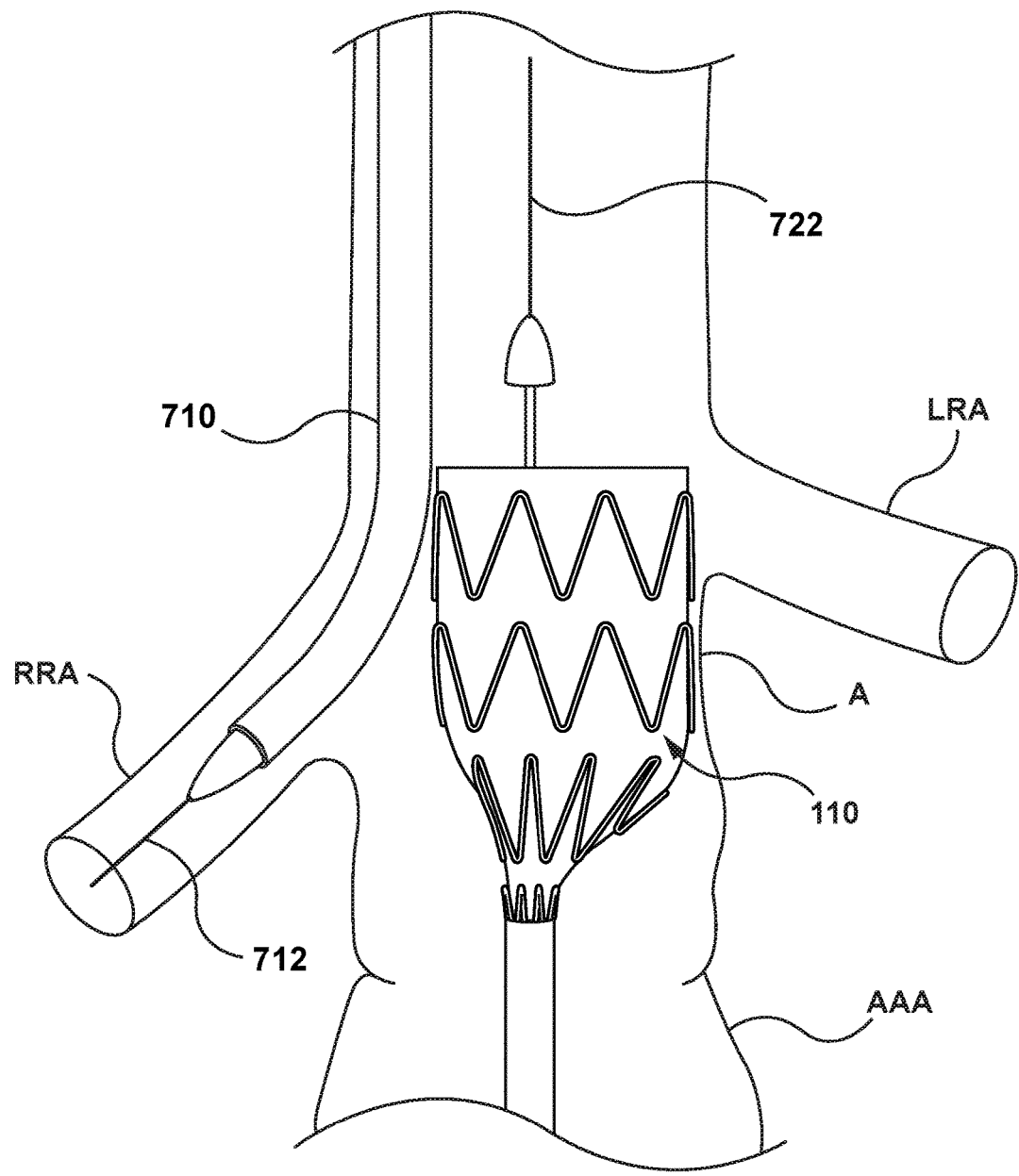

The method 1000 can also include a step of deploying the exclusion structure 110 (e.g. main stent-graft) from the second delivery catheter 720 (block 1006). In an example of this step, a sheath of the second delivery catheter is retracted, enabling the exclusion structure 110 to self-expand within the main vessel (e.g. the aorta A). FIG. 11B shows the sheath of the second delivery catheter 720 being retracted and the exclusion structure 110 partially expanded. In an embodiment, the first delivery catheter 710 is in place prior to this step. Otherwise, it would be difficult to advance the first delivery catheter 710 outside of an expanded exclusion structure 110. In another embodiment, a sheath or tube (not shown) may be placed in aorta adjacent the preferred "landing zone" or "seal zone" prior to deployment of the exclusion structure 110. First delivery catheter 710 may then be advanced through the sheath after the exclusion structure 110 has been deployed. A proximal portion 122 of the exclusion structure 110 can be positioned adjacent to the preferred "landing zone" or "seal zone" upstream of the target tissue defect. The central portion 126 of the exclusion structure 110 can be aligned with the target tissue defect in the main blood vessel, as shown in FIG. 11B.

Figure 11C:
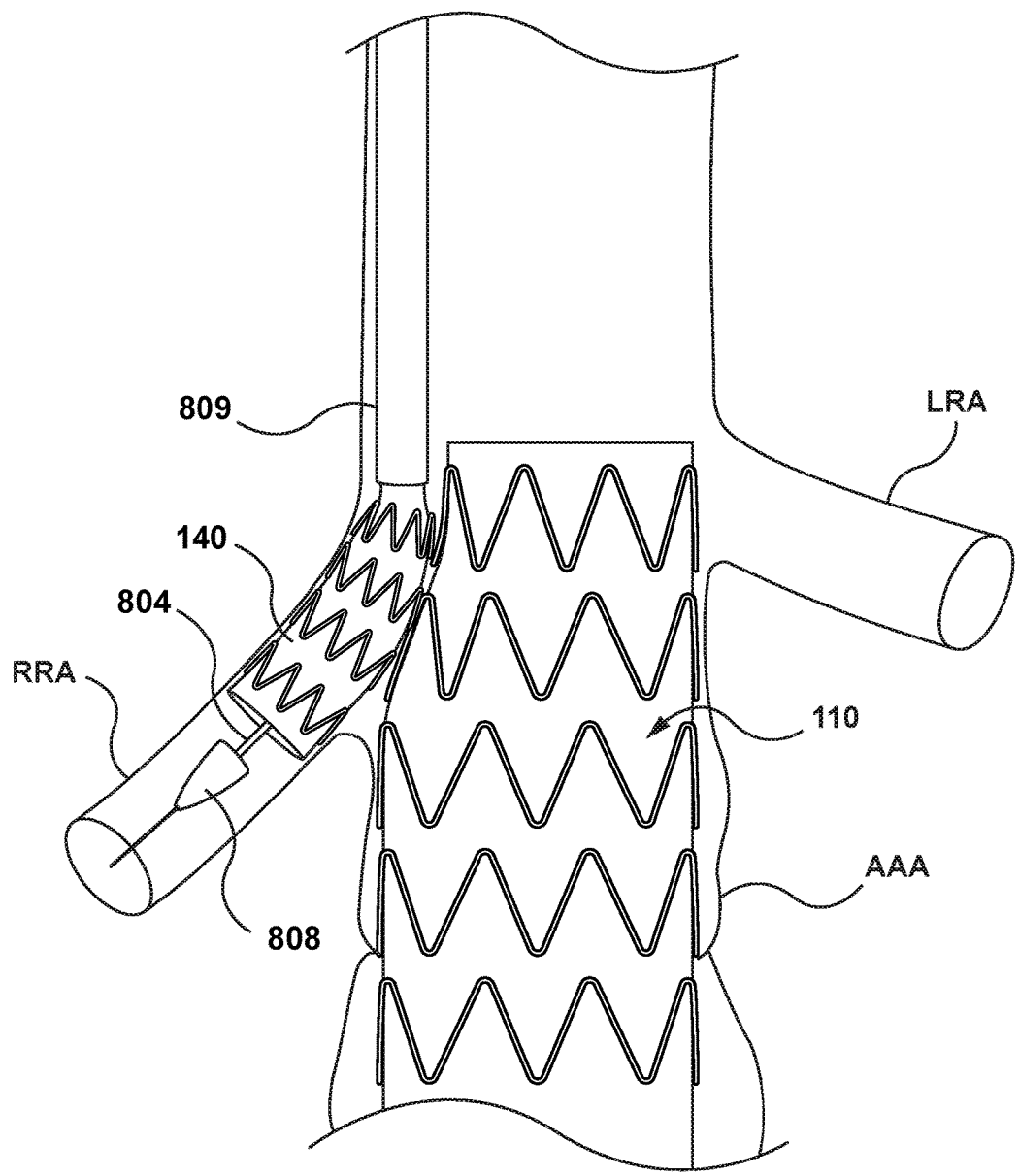

The method 1000 can further include expanding the branch assembly 130 to a deployed configuration (block 1008). This step can include deploying the outer branch prosthesis 140 such that the second portion 144 that is deployed within the branch vessel BV and having the first portion 142 is deployed within the main vessel such that the inflow region 150 at the upstream portion 148 is oriented in an upstream direction adjacent the exclusion structure 110 (block 1010). In some embodiments, the outer branch prosthesis 140 is self-expanding and the step of deploying the outer branch prosthesis 140 includes retracting the sheath 809 of the first delivery catheter 710, as shown in FIGS. 11C-11D.

Figure 11D:
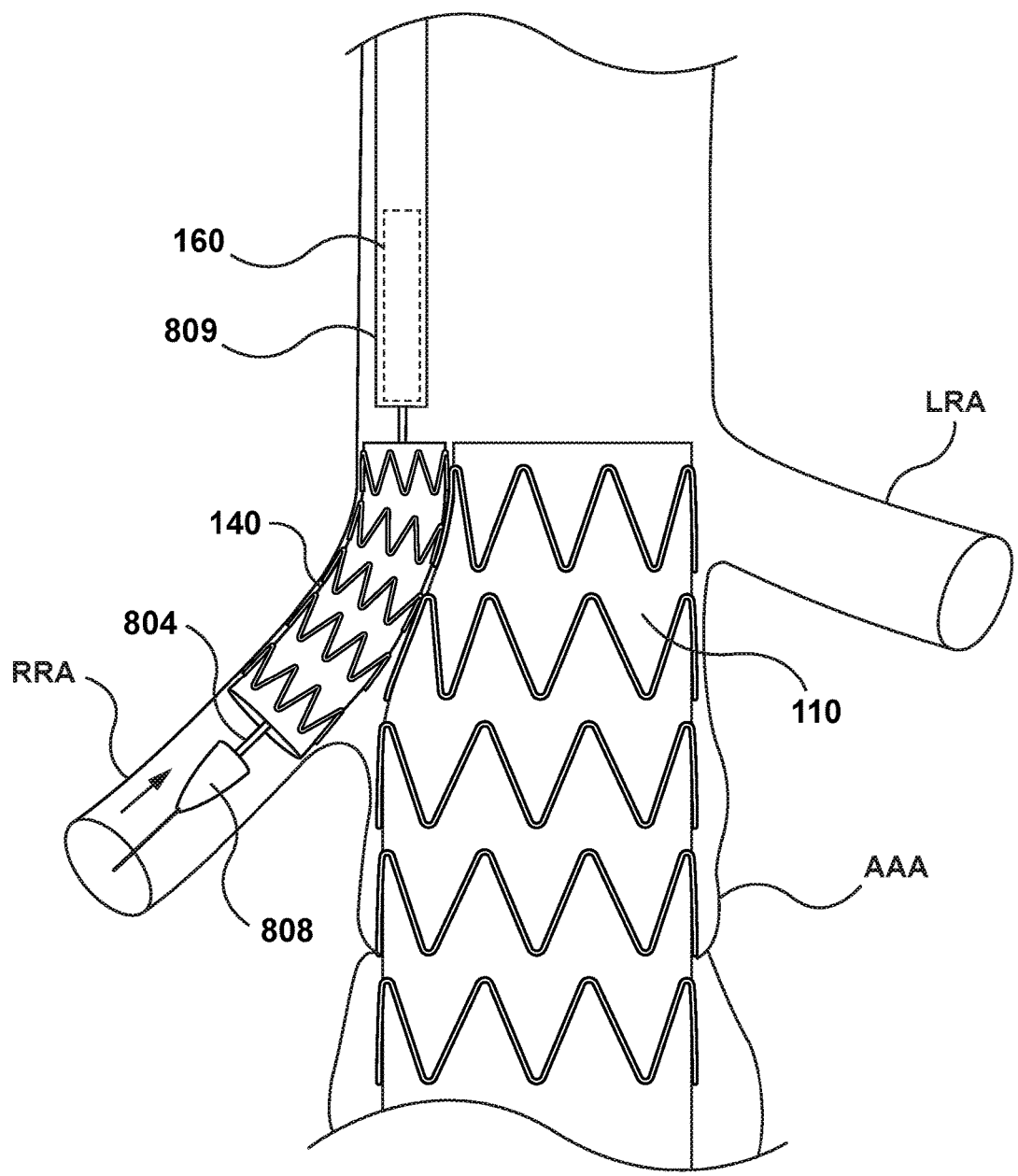
Figure 11E:
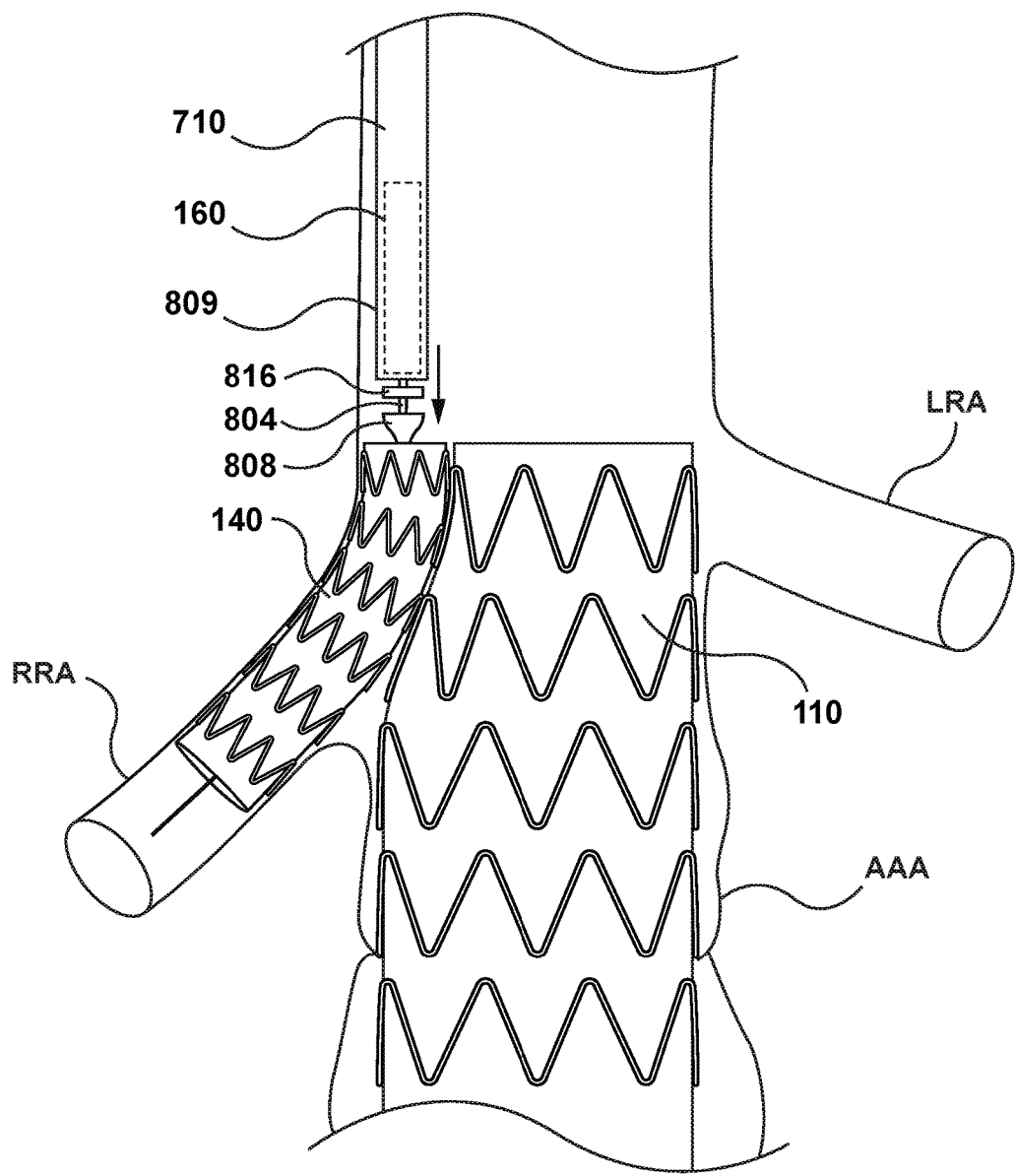

In some embodiments, after deployment of the outer branch prosthesis 140, the distal tip 808 is in the branch vessel BV distal of the outer branch prosthesis 140, and the support structure 160 is in the main vessel proximal of the outer branch prosthesis 140, as shown in FIG. 11D. If the entire delivery catheter 710 is advanced distally to advance the support structure to a location within the outer branch prosthesis 140, the distal tip 808 will be advanced further into the branch vessel BV, which may be undesirable. Therefore, in some embodiments, the method 1000 can include retracting proximally the inner member 804, and hence also the distal tip 808 attached thereto (block 1012). The arrow in FIG. 11D indicates retracting the inner member 804 with the distal tip 808 attached thereto. Therefore, in some embodiments, the distal tip 808 after being retracted is disposed adjacent to the stent stop 816, as shown in FIG. 11E. This permits advancement of the first delivery catheter 710, or portions thereof, without advancing the distal tip 808 too far into the branch vessel BV.

Figure 11F:
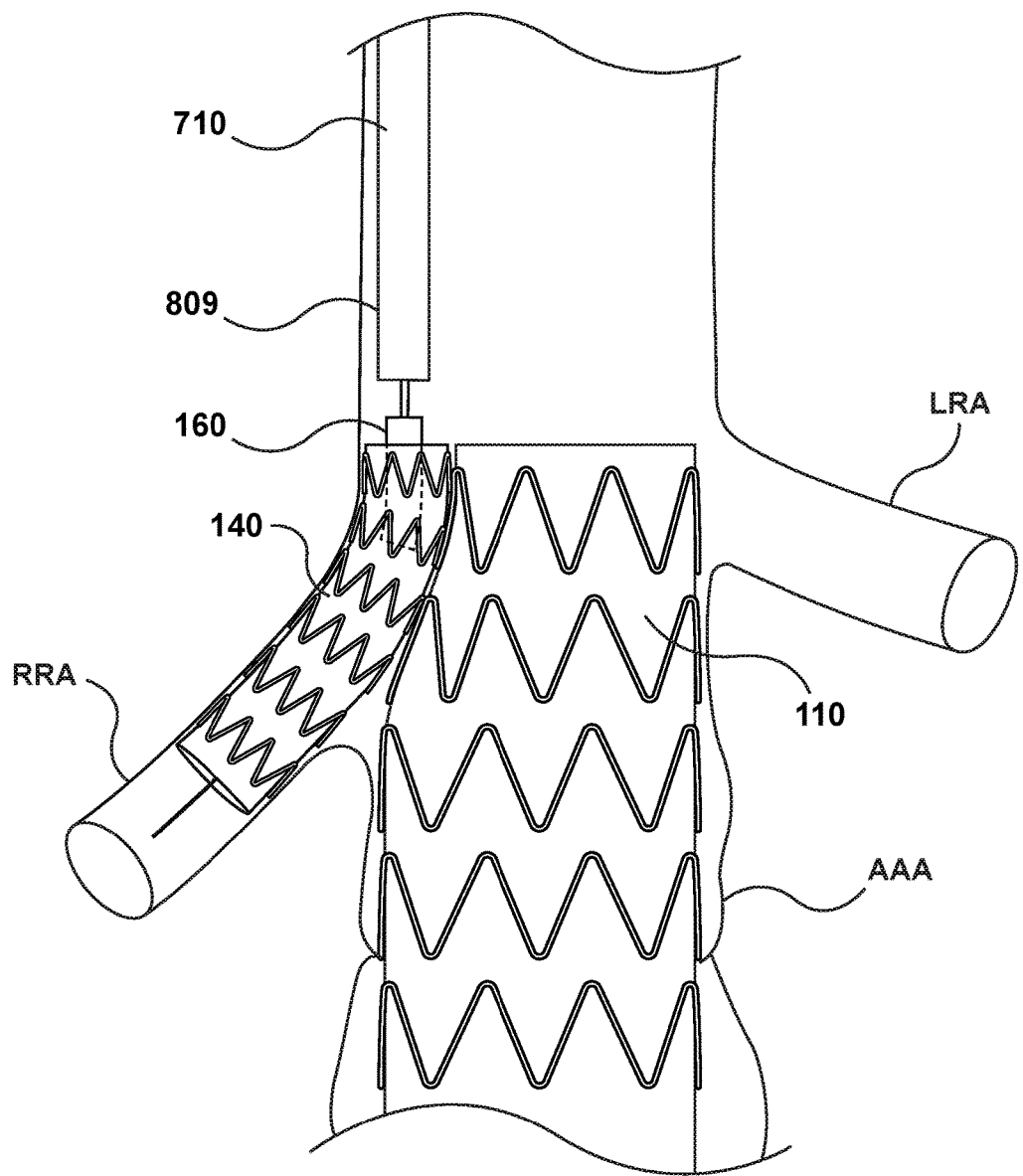

The method 1000 can also include advancing the first delivery catheter 710 into the deployed outer branch prosthesis 140 to position the support structure 160 at least partially within inflow region 150 of the outer branch prosthesis, as indicated by the arrow in FIG. 11E (block 1014). In some embodiments, the entire first delivery catheter 710 is advanced distally and then the sheath 809 is retracted to expose the support structure 160 and the balloon 814, as shown in FIG. 11F. In some embodiments, the sheath 809 may not be advanced, and the shaft 805/guidewire shaft 905 is advanced with the balloon 814 and the support structure 160 mounted thereon, as shown in FIG. 11F. In embodiments with a self-expanding support structure 160, the sheath 809 must be advanced with the support structure 160. As explained above, in some embodiments, it may be desirable to position the support structure 160 such that a distal portion of the support structure 160 extends distally beyond the inflow region 150 of the outer branch prosthesis 140, but still within the main vessel.

Figure 11G:
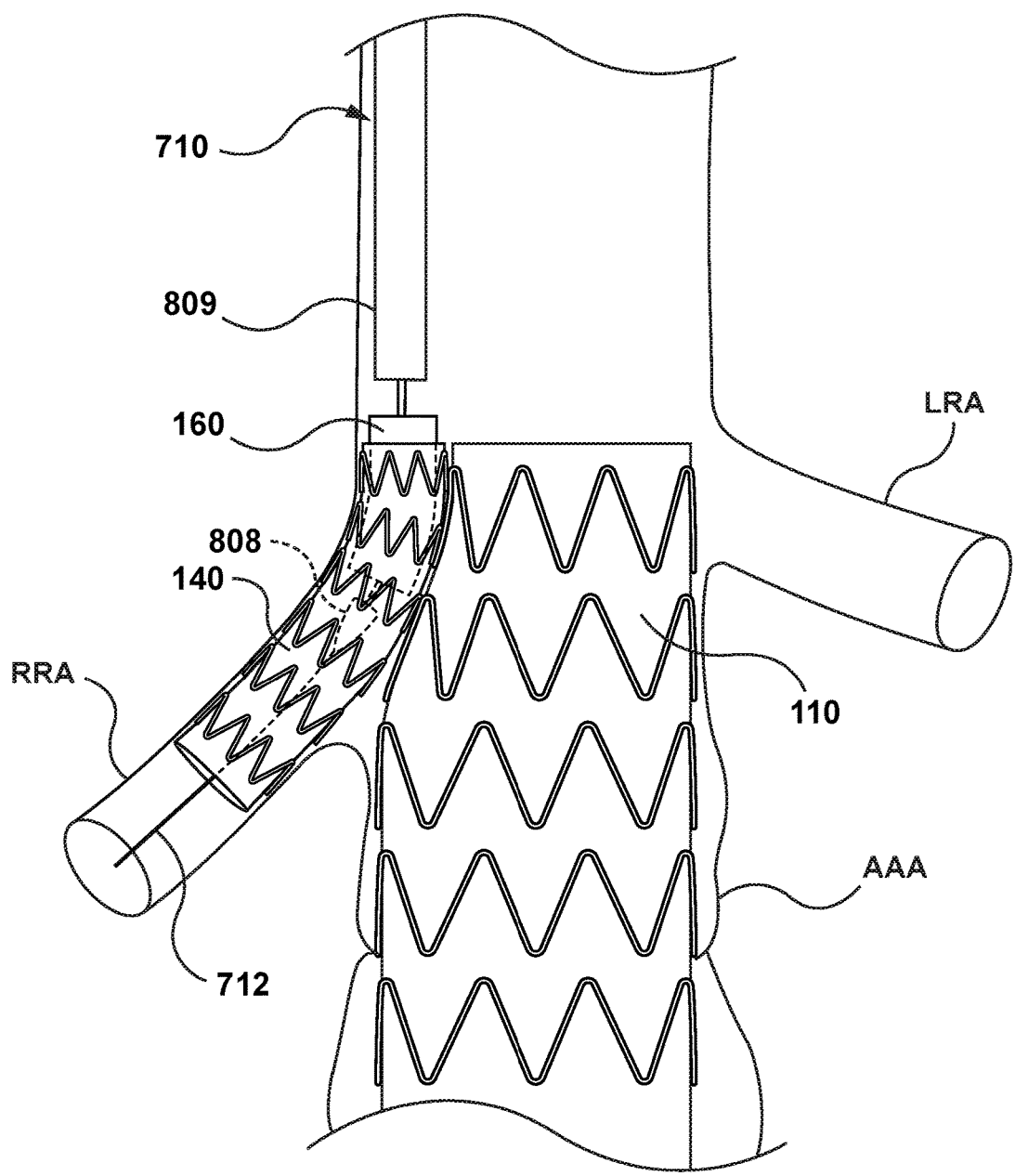

The method 1000 can also include deploying the support structure 160 at least partially disposed within the inflow region 150 of the outer branch assembly 160 (block 1016). In some embodiments, this step can include injecting inflation fluid into the inflation lumen 812/912 to inflate the balloon 814, thereby radially expanding the support structure 160. In other embodiments utilizing a self-expanding support structure 160, the sheath 809 is retracted to enable the support structure to self-expand. FIG. 11G shows the support structure 160 deployed within the inflow region 150 of the outer branch prosthesis 140.

The method 1000 can further include withdrawing the delivery catheters 710, 720 from the patient (block 1018). The delivery catheters 710, 720 may be withdrawn when the devices within them are deployed, or may be withdrawn at the end of the procedure. This leaves the prosthetic assembly 100 deployed at the target tissue as shown in FIGS. 2A and 2B.

As explained above, the combination of compression forces $F_C$ exerted by the exclusion structure 110 and the inner wall W acting against the outward radial force of the outer branch assembly 140 enables the outer branch assembly 140 to at least partially deform to fill gaps or gutters G formed by partial deformation of the exclusion structure 110. Further, the support structure 160 supports the outer branch assembly 140 such that the deformation of the outer branch assembly 140 does not block blood flow through the internal conduit 132. Thus, the support structure 160 maintains patency of the outer branch assembly 140 such that sufficient blood flows to the branch vessel BV. Features of the endoluminal prosthetic assemblies and delivery system components described above and illustrated in FIGS. 2A-9C can be modified to form additional embodiments configured in accordance with the present technology. For example, the delivery system 700 can provide delivery of any of the endoluminal prosthetic assemblies 100 illustrated in FIGS. 2A-9C using one or more additional delivery elements such as straightening sheaths and/or guide wires controllable, for example, using an operator-controlled handle (not shown). Similarly, the endoluminal prosthetic assemblies 100 described above and illustrated in FIGS. 2A-9C showing the support structure having only a circular cross-sectional profile can also include a support structure having other non-circular cross-sectional profiles. Additionally, while endoluminal prosthetic assemblies 100 described above show two branch stent assemblies 130, it will be understood that the endoluminal prosthetic assembly 100 can include one branch stent assembly 130, or in other embodiments, additional branch stent assemblies 130 for preserving blood flow to several affected branch vessels originating within or near a target tissue defect.

Various method steps described above for delivery and deployment of the prosthetic assembly for repairing a target tissue defect in a blood vessel of a patient also can be interchanged to form additional embodiments of the present technology. For example, while the method steps described above are presented in a given order, alternative embodiments may perform steps in a different order. For example, and not by way of limitation, the method 1000 describes expansion of the exclusion structure prior to deployment of the branch assembly. However, in some embodiments, the branch assembly may be at least partially deployed prior to expansion of the exclusion structure. The various embodiments described herein may also be combined to provide further embodiments.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A prosthetic assembly for repairing a target tissue defect within a target vessel region in a patient, the prosthetic assembly comprising:
    an exclusion structure sized to substantially cover the target tissue defect in the target vessel region when the exclusion structure is in a deployed configuration; and
    a branch assembly for directing fluid flow to a branch vessel from the target vessel region, the branch assembly comprising,
        an outer branch prosthesis having a first portion and a second portion, wherein the first portion is configured to be deployed between the exclusion structure and a wall of the target vessel region, and the second portion is configured to be deployed in the branch vessel branching from the target vessel region, the first and second portions of the outer branch prosthesis including a stent and graft material, and
        a support structure at least partially disposed within the outer branch prosthesis at the first portion when the branch assembly is in a deployed configuration,
        wherein an inflow region of the first portion of the outer branch prosthesis is expandable to a cross-sectional dimension larger than a cross-sectional dimension of the support structure, and wherein the first portion is deformable to a non-circular cross-sectional shape when deployed.

2. The prosthetic assembly of claim 1, wherein the inflow region is configured to deform to the non-circular cross-sectional shape to conform to the wall of the target vessel region and an outer surface of the exclusion structure.

3. The prosthetic assembly of claim 1, wherein the cross-sectional shape of the support structure remains sufficiently stable when the inflow region of the outer branch prosthesis is deformed to the non-circular cross-sectional shape.

4. The prosthetic assembly of claim 3, wherein the support structure is substantially circular in cross-section to maintain patency of the first portion of the outer branch prosthesis.

5. The prosthetic assembly of claim 1, wherein at least a portion of the stent at the first portion of the outer branch prosthesis comprises two or more posts oriented lengthwise along the first portion, and wherein the posts provide a deformation orientation plane such that when deformed, the cross-sectional shape is substantially elliptical.

6. The prosthetic assembly of claim 1, wherein the inflow region is configured to be deformable to an oval cross-sectional shape by the exclusion structure when the prosthetic assembly is deployed at the target vessel region.

7. The prosthetic assembly of claim 1, wherein the inflow region has a first cross-sectional dimension and the second portion has a second cross-sectional dimension less than the first cross-sectional dimension.

8. The prosthetic assembly of claim 1, wherein the support structure has a central longitudinal axis and a first radial strength oriented in an outward, radial direction from the central longitudinal axis, and wherein the first portion of the outer branch prosthesis has a second radial strength oriented in an outward, radial direction from the central longitudinal axis, and wherein the second radial strength is less than the first radial strength.

9. The prosthetic assembly of claim 1, wherein the first portion of the outer branch prosthesis has a central longitudinal axis, and wherein the support structure is configured to be deployed coaxially with the first portion of the branch stent along the central longitudinal axis.

10. The prosthetic assembly of claim 1, wherein the support structure is a balloon-expandable stent.

11. The prosthetic assembly of claim 1, wherein the support structure is a self-expanding stent.

12. The prosthetic assembly of claim 1, wherein the exclusion structure is an endoprosthetic stent-graft and a proximal portion of the branch assembly is configured to be deployed in parallel with a proximal portion of the endoprosthetic stent-graft.

13. The prosthetic assembly of claim 12, wherein the target tissue defect is an abdominal aortic aneurysm, and wherein the endoprosthetic stent-graft is configured to be implanted in the aorta in a manner to bypass the aneurism.

14. The prosthetic assembly of claim 1, further comprising a second branch assembly for directing fluid flow to a second branch vessel from the target vessel region.

15. The prosthetic assembly of claim 1, wherein the support structure includes an upstream end and a downstream end, and wherein the upstream end extends a distance in an upstream direction beyond a proximal end of the first portion of the outer branch prosthesis.

16. The prosthetic assembly of claim 1, wherein the inflow region of the outer branch prosthesis includes a rim at a proximal end of the inflow region, the rim having an undeformed configuration, the undeformed configuration having a generally circular shape.

17. The prosthetic assembly of claim 1, wherein the support structure has a longitudinal axis, and wherein the inflow region of the outer branch assembly in a radially expanded, unconstrained configuration flares outward from the longitudinal axis by a taper angle.

18. The prosthetic assembly of claim 17, wherein the taper angle continuously changes between a transition point of the inflow region and a rim at a proximal end of the inflow region.

19. The prosthetic assembly of claim 1, wherein:
    the first portion of the outer branch prosthesis includes a plurality of first struts interconnected around a circumference of the first portion;
    the support structure includes a plurality of second struts interconnected around a circumference of the support structure; and
    the second struts are more rigid than the first struts.

20. The prosthetic assembly of claim 1, wherein the first portion of the outer branch prosthesis has a frustoconical shape in a radially expanded, unconstrained configuration.

21. The prosthetic assembly of claim 1, wherein the exclusion structure is configured to provide a compressive force against the branch assembly, and wherein the compressive force is sufficient to deform the outer branch prosthesis without substantially deforming the support structure deployed within the outer branch prosthesis.

22. The prosthetic assembly of claim 1, wherein a distal end of the second portion of the outer branch prosthesis is open to permit fluid flow therethrough.

* * * * *